United States Patent
Watson et al.

(10) Patent No.: US 6,677,428 B1
(45) Date of Patent: *Jan. 13, 2004

(54) MAMMAGLOBIN, A SECRETED MAMMARY-SPECIFIC BREAST CANCER PROTEIN

(75) Inventors: Mark A. Watson, St. Louis, MO (US); Timothy P. Fleming, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/509,015

(22) PCT Filed: Mar. 25, 1999

(86) PCT No.: PCT/US99/17991

§ 371 (c)(1), (2), (4) Date: May 30, 2000

(87) PCT Pub. No.: WO99/14230

PCT Pub. Date: Mar. 25, 1999

Related U.S. Application Data

(63) Continuation-in-part of application No. PCT/US96/08235, filed on May 31, 1996, which is a continuation-in-part of application No. 08/455,896, filed on May 31, 1995, now Pat. No. 5,668,267.

(51) Int. Cl.[7] ........................ A61K 38/00; A61K 39/00
(52) U.S. Cl. ................. 530/300; 424/184.1; 424/185.1; 424/198.1
(58) Field of Search ................................ 530/300, 350; 424/184.1, 185.1, 198.1

(56) References Cited

U.S. PATENT DOCUMENTS

| | | | |
|---|---|---|---|
| 5,298,399 A | * | 3/1994 | Uozumi et al. |
| 5,573,916 A | | 11/1996 | Cheronis et al. |
| 5,593,972 A | | 1/1997 | Weiner et al. |
| 5,610,031 A | | 3/1997 | Burgeson et al. |
| 5,668,267 A | | 9/1997 | Watson |
| 5,855,889 A | * | 1/1999 | Watson et al. |
| 5,922,836 A | * | 7/1999 | Watson et al. |

FOREIGN PATENT DOCUMENTS

WO   WO96/38463   12/1996

OTHER PUBLICATIONS

Holmes (Exp. Opin. Invest. Drugs, 2001, 10(3):511–519).*
Taber's Cyclopedic Medical Dictionary, F.A. Davis Co., Philadelphia, 1989, p 41.*
Herbert et al (Dictionary of Immunology, 4th Ed., Academic Press, London, 1985, p. 11).*
Allred et al., Journ. of the Nat'l Cancer Inst., vol. 85, *Association of p53 Protein Expression with Tumor Cell Proliferation Rate and Clinical Outcome in Node–Negative Breast Cancer*, pp. 200–206, Feb. 3, 1993.
Bagshawe, Adv. in Pharm., vol. 24, *Antibody–Directed Exzyme Prodrug Therapy (ADEPT)*, pp. 99–121, 1993.
Bjork et al., Anticancer Research 11, *Expression and Partial Characterization of Estramustine–Binding protein (EMBP) in Human Breast Cancer and Malignant Melanoma*, pp. 1173–1182, 1991.
Bjork et al., Cancer Research vol. 42, *Partial Characterization and "Quantitation" of Human Prostatic Estramustine–binding Protein*, pp. 1935–1942, May 1982.
Borras–Cuesta, Eur.J. Immunol., vol. 17, *Engineering of immunogenic peptides by co–linear synthesis of determinants recognized by B and T cells*, pp. 1213–1215, 1987.
Burgess et al., Journ. of Cell Bio., vol. 111, *Possible Dissociation of the Heparin–binding and Mitogenic Activities of Heparin–binding (Acidic Fibroblast)Growth Factor–1 from Its Receptor–binding Activities by Site–directed Mutagenesis of a Single Lysine Residue*, pp. 2129–2138, 1990.
Cato et al., Anticancer Research, vol. 5, *The Hormonal Regulation of Uteroglobin Gene Expression*, pp. 65–72, 1985.
Denton et al., Cancer Letters, vol. 70, *Inducation of antibody responses to breast carcinoma associated mucins using synthetic peptide constructs as immunogens*, pp. 143–150, 1993.
Falk et al., Nature vol. 351, *Allele–specific motifs revealed by sequencing of self–peptides eluted form MHC molecules*, pp. 290–296, May 23, 1991.
Good et al., Science, vol. 235, *Construction of Synthetic Immunogen: Use of New T–Helper Epitope on Malaria Circumsporozoite Protein*, pp. 1059–1062, Feb. 27, 1987.
Hammer et al., J. Exp. Med., *Identification of a Motif for HLA–DR1 Binding Peptides Uising M13 Display Llbraries*, pp. 1007–1013, 1992.
Henderson et al., Science, vol. 255, *HLA–A2. 1–Associated Peptides from a Mutant Cell Line: A Second Pathway of Antigen Presentation*, pp. 1264–1266, 1992.

(List continued on next page.)

Primary Examiner—Susan Ungar
(74) Attorney, Agent, or Firm—Thompson Coburn LLP

(57) ABSTRACT

A purified and isolated DNA sequence and the encoded mammary-specific secreted protein, mammaglobin, are disclosed. Also disclosed are methods for detecting breast cancer based upon the overexpression and secretion of mammaglobin by breast cancer cells. The methods detect and/or quantitate the presence of mammaglobin or the mRNA encoding mammaglobin. Immunotherapy-based methods for treating a breast cancer patient with a mammaglobin-expressing tumor are also disclosed. The methods involve using mammaglobin antigens to induce a humoral and/or cell-mediated immune response against the tumor.

12 Claims, 12 Drawing Sheets

OTHER PUBLICATIONS

Hill et al., Nature, vol. 360, *Molecular analysis of the association of HLA–B53 and resistance to severe malaria*, pp. 434–439, Dec. 3, 1992.

Lazar et al., Molecular and Cellular Bio., *Transforming Growth Factor : Mutation of Aspartic Acid 47 and Leucine 48 Results in Different BIological Activities*, pp. 1247–1252, Mar., 1988.

LoBuglio et al., Amer. Journ. of the Med. Sci., vol. 304, No. 3, *Advances in Monoclonal Antibody Therapy of Cancer*, pp. 214224, Sep., 1992.

Maroulakou et al., Proc. Natl. Acad. Sci. USA, vol. 91, *Prostate and mammary adenocarcinoma in transgenic mice carrying a rat C3(1) simian virus 40 large tumor antigen fusion gene*, pp. 11236–11240, Nov. 1994.

Miele et al., J. Endocrinol. Invest. vol. 17, *Uteroglobin and Uteroglobin–like proteins; The uteroglobin family of proteins*, pp. 679–692, 1994.

Miele et al., Endocrine Rev., vol. 8, No. 4, *Uteroglobin: Structure, Molecure Biology, and New Perspectives on Its Function as a Phospholipase $A_2$ Inhibitor*, pp. 474–490, 1987.

Panina–Bordignon et al., Eur. J. Immunol. vol. 19, *Universally immunogenic T cell epitopes: promiscuous binding to human MHC class II and promiscuous recognition by T cells*, pp. 2237–2242, 1989.

Parker et al., Annals N. Y. Acad. of Sci. vol. 438, *Organization and Expression of Genes Encoding Prostatic Steroid Binding Protein*, p. 115–124, 1984.

Parker et al., J. Steroid Biochem., Vol 20, No. 1, *Organization and Expression of Prostatic Steroid Binding Protein Genes*, pp. 67–71, 1984.

Peeters et al., Eur.J. Biochem. vol. 115, *Structural Studies on Rat Prostatic Binding Protein*, pp. 115–121, 1981.

Peoples et al., Proc. Natl. Acad. Sci. USA, vol. 92, *Breast and ovarian cancer–specific cytotoxic T lymphocytes recognize the same HEr2/neu–derived peptide*, pp. 432–436, Jan. 1995.

Peri et al., Journ. of Clin. Invest., vol. 92, *Tissue–specific Expression of the Gene Coding for Human Clara Cell 10–kD Protein, a Phospholipase $A_2$–inhibitority Protein*, pp. 2099–2109, Nov., 1993.

Sandmoeller et al., Oncogene vol. 9, *The uteroglobin promoter targets expression of the SV40 T antigen to a variety of secretory epithelial cells in transgenic mice*, pp. 2805–2815, 1994.

Schoenfeld et al., Cancer Research 54, *Detection of Breast Cancer Micrometastases in Axillary Lymph Nodes by Using Polymerase Chain Reaction*, pp. 2986–2990, 1994.

Slamon et al., Science, vol. 244, *Studies of the HER–2/neu Proto–oncogene in Human Breast and Ovarian Cancer*, pp. 707–712, May 12, 1989.

Tao et al., Journ. of Immun., vol. 143, *Studies of Aglycosylated Chimeric Mouse–Huma IgG*, pp. 2595–2601, 1989.

Taylor et al., Virology, vol. 187, *Nonreplicating Viral Vectors as Potential Vaccines; Recombinant Canarypox Virus Expressing Measles Virus Fusion (F) and Hemagglutinin (HA) Glycoproteins*, pp. 321–328, 1992.

Thor et al., Journ. of the Nat'l Cancer Inst., vol. 84, No. 11, *Accumulation of p53 Tumor Suppressor Gene Protein; An Independent Marker of Prognosis in Breast Cancer*, Jun. 3, 1992.

Toso et al., Cancer Research, vol. 56, *MAGE–1–specific Precursor Cytotoxic T–Lymphocytes Present among tumor–infiltrating Lymphocytes from a Patient with Breast Cancer: Characterization and Antigen–specific Activation*, pp. 16–20, Jan. 1, 1996.

Watson et al., Cancer Research 54, *Isolation of Differentially Expressed Sequence Tags from Human Breast Cancer*, pp. 4598–4602, Sep. 1, 1994.

Watson et al., Cancer Research, vol. 56, Mammaglobin, a Mammary–specific Member of the Uteroglobin Gene Family, Is Overexpressed in Human Breast Cancer[1], pp. 860–865, 1996.

\* cited by examiner

|     | 9   | 18  | 27  | 36  | 45  | 54  |
|-----|-----|-----|-----|-----|-----|-----|
5' GAC AGC GGC TTC CTT GAT CCT TGC CAC CCG CGA CTG AAC ACC GAC AGC AGC AGC

|     | 63  | 72  | 81  | 90  | 99  | 108 |
|-----|-----|-----|-----|-----|-----|-----|

CTC ACC ATG AAG TTG CTG ATG GTC CTC ATG CTG GCG GCC CTC TCC CAG CAC TGC
        Met Lys Leu Leu Met Val Leu Met Leu Ala Ala Leu Ser Gln His Cys
        1                                   10

|     | 117 | 126 | 135 | 144 | 153 | 162 |
|-----|-----|-----|-----|-----|-----|-----|

TAC GCA GGC TCT GGC TGC CCC TTA TTG GAG AAT GTG ATT TCC AAG ACA ATC AAT
Tyr Ala Gly Ser Gly Cys Pro Leu Leu Glu Asn Val Ile Ser Lys Thr Ile Asn
            20                                  30

|     | 171 | 180 | 189 | 198 | 207 | 216 |
|-----|-----|-----|-----|-----|-----|-----|

CCA CAA GTG TCT AAG ACT GAA TAC AAA GAA CTT CTT CAA GAG TTC ATA GAC GAC
Pro Gln Val Ser Lys Thr Glu Tyr Lys Glu Leu Leu Gln Glu Phe Ile Asp Asp
                40                                  50

|     | 225 | 234 | 243 | 252 | 261 | 270 |
|-----|-----|-----|-----|-----|-----|-----|

AAT GCC ACT ACA AAT GCC ATA GAT GAA TTG AAG GAA TGT TTT CTT AAC CAA ACG
Asn Ala Thr Thr Asn Ala Ile Asp Glu Leu Lys Glu Cys Phe Leu Asn Gln Thr
                        60                                          70

|     | 279 | 288 | 297 | 306 | 315 | 324 |
|-----|-----|-----|-----|-----|-----|-----|

GAT GAA ACT CTG AGC AAT GTT GAG GTG TTT ATG CAA TTA ATA TAT GAC AGC AGT
Asp Glu Thr Leu Ser Asn Val Glu Val Phe Met Gln Leu Ile Tyr Asp Ser Ser
                                    80

|     | 333 | 342 | 351 | 360 | 369 | 378 |
|-----|-----|-----|-----|-----|-----|-----|

CTT TGT GAT TTA TTT TAA CTT TCT GCA AGA CCT TTG GCT CAC AGA ACT GCA GGG
Leu Cys Asp Leu Phe ***
        90

|     | 387 | 396 | 405 | 414 | 423 | 432 |
|-----|-----|-----|-----|-----|-----|-----|

TAT GGT GAG AAA CCA ACT ACG GAT TGC TGC AAA CCA CAC CTT CTC TTT CTT ATG

|     | 441 | 450 | 459 | 468 | 477 | 486 |
|-----|-----|-----|-----|-----|-----|-----|

TCT TTT TAC TAC AAA CTA CAA GAC AAT TGT TGA AAC CTG CTA TAC ATG TTT ATT

|     | 495 |     |     |     |     |     |
|-----|-----|-----|-----|-----|-----|-----|

TTA ATA AAT TGA TGG CA 3'

Figure 2

```
hCC10  -21  MKLAVTLTLVTLALCCSSASAEICPSFQRVIETLLMDTPSS-
hMaM    01  MKLLMVLMLAALSQHCY--A-GSGCPLLENVISKTINPQVSKT
rPSC3   01  MKLVFLFLLVTIPICCY-ASGSGCSILDEVIRGTINSTVTLH hCC10   20  -YEAAMELFSPDQDMREAGAQLKKLVDTLPQK---PRESIIKL
hMaM    41  EYKELLQEFIDDNATTNAIDELKECF---LNQTDETLSNVEVF
rPSC3   42  DYMKLVKPYVQDHFTEKAVKQFKQCF---LDQTDKTLENVGVM hCC10   61  MEKIAQSSLCN
hMaM    82  MQLIYDSSLCDLF
rPSC3   83  MEAIFNSESCQQPS
```

Figure 3

MAMMAGLOBIN, A SECRETED MAMMARY-SPECIFIC BREAST CANCER PROTEIN

RELATED APPLICATIONS

This application is a continuation-in-part of PCT/US96/08235, filed May 31, 1996 which is a continuation-in-part of U.S. application Ser. No. 08/455,896, filed May 31, 1995, now U.S. Pat. No. 5,668,267, issued on Sep. 16, 1997.

BACKGROUND OF THE INVENTION (1) Field of the Invention

This invention relates generally to the field of breast cancer pathogenesis and, more particularly, to a cDNA sequence and encoded mammary-specific protein for use in detecting and treating breast cancer.

(2) Description of the Related Art

Breast cancer is one of the most common and potentially lethal of cancers.

Although early diagnosis and treatment can reduce morbidity and mortality related to the disease, the positive predictive value of mammography has been estimated to be only about 25% (Hall et al., *N Engl J Med* 327:319–328, 1992 which is incorporated by reference). It would, therefore, be desirable to have a means for detecting the cancer earlier than the cancer can be detected using mammography and a genetic or biochemical marker might be able to provide such means to complement and increase the predictive value of mammography. (Hayes, *Hematol Oncol Clin N Am* 8:485, 1994 which is incorporated by reference).

The development of breast cancer is accompanied by a number of genetic changes (For review see Porter-Jordan, *Hematol Oncol Clin N Am* 8:73, 1994 which is incorporated by reference). Such changes include gross chromosomal alterations and loss of genetic markers (Devilee et al, *Biochim Biophys Acta* 1198:113, 1994; Callahan et al, *J Cell Biochem Suppl* 17:167, 1993 which are incorporated by reference). The progression of breast neoplasia has also been shown to result in qualitative and quantitative changes in expression of previously identified genes that encode growth factors and their receptors (Zajchowski et al., *Cancer Res* 48:7041, 1988 which is incorporated by reference), structural proteins (Trask et al., *Proc Natl Acad Sci* 87:2319, 1990 which is incorporated by reference), second messenger proteins (Ohuchi et al., *Cancer Res* 26:2511, 1986 which is incorporated by reference), and transcription factors (Harris, *Adv Cancer Res* 59:69:1992 which is incorporated by reference). These changes in gene expression could potentially form the basis for developing a breast cancer marker, although the precise role of these gene changes in the pathogenesis of breast carcinoma in patient biopsy samples is not well understood.

In addition to providing a genetic or biochemical marker for breast cancer for early detection of the disease, it would also be desirable to have a tumor marker that might provide an estimation of prognosis, a means for selection and evaluation of therapy and a means for the targeting of therapy. Although a number of tissue markers have been identified, none are sufficiently sensitive or tumor specific to be ideally suited for diagnosis or for screening the general population. (Id.). Thus, there remains a continuing need for a breast cancer marker such as a gene along with its expressed protein that can be used to specifically and selectively identify the appearance and pathogenic development of breast cancer in a patient, and that can be used in tumor-specific immunotherapy.

Using a modified differential display polymerase chain reaction technique to isolate differentially expressed sequence tags from mammary carcinoma, several sequence fragments were isolated that were uniquely expressed in neoplastic mammary epithelial tissue as compared to normal tissue controls (Watson and Fleming, *Cancer Res* 54:4598–4602, 1994 which is incorporated by reference). The discovery of one of these sequence tags identified as DEST002 has led to the discovery and isolation of the novel full length cDNA and encoded protein now referenced as mammaglobin. The cDNA and protein are both new.

SUMMARY OF THE INVENTION

Briefly, therefore, the present invention is directed to the identification of novel genes whose expression is increased in breast cancer and to the isolating of cDNA's from the mRNA's of these genes. Accordingly, applicants have succeeded in discovering a novel cDNA and the encoded mammary-specific secretory protein, mammaglobin. The cDNA is in purified and isolated form and has a nucleotide sequence identified as SEQ ID NO:1 and the encoded protein, mammaglobin, is in purified and isolated form and has an amino acid sequence identified as SEQ ID NO:2.

Mammaglobin is overexpressed in 27% of stage I primary breast cancer tumors. This suggests that dysregulation of the mammaglobin gene occurs early and frequently in breast cancer. The discovery of mammaglobin and its cDNA, therefore, provide the basis for the development of novel methods and compositions for the detection and treatment in humans and other mammals.

Thus, the present invention is directed to novel methods for detecting the presence of breast neoplasia cells in a sample. In one embodiment, cDNA encoding mammaglobin or a derivative of said cDNA is used to detect the presence of mammaglobin mRNA in a sample. The method comprises the steps of: (a) providing a polynucleotide containing a nucleotide sequence having the sequence of SEQ ID NO:1 or a derivative thereof, (b) incubating the nucleotide sequence with the sample under conditions in which the sequence can hybridize with mRNA from breast neoplasia cells, and (c) detecting the existence of a DNA-RNA hybridization complex.

Another aspect of the present invention provides a kit for detecting the presence of breast neoplasia cells in a sample by hybridization. The kit comprises a polynucleotide containing a nucleotide sequence having the sequence of SEQ ID NO:1 or a derivative thereof packaged in a container.

In another embodiment of the present invention, mammaglobin expression in a sample is determined by detecting the presence of cDNA that is reverse transcribed from mammaglobin mRNA in the sample. The method comprises the steps of: (a) producing a cDNA encoding mammaglobin from mRNA using the reverse transcription method in a sample obtained from a patient, (b) providing two primers for the polymerase chain reaction method which comprise oligomers that flank or lie within the cDNA encoding mammaglobin, and (c) amplifying the cDNA encoding mammaglobin by the polymerase chain reaction method. The two primers have nucleotide sequences comprising SEQ ID NO:3 and SEQ ID NO:4.

Another embodiment to the present invention provides a kit for detecting the presence of breast neoplasia cells in a sample by the polymerase chain reaction. The kit comprises two primers for the polymerase chain reaction method which comprise oligomers that flank or lie within a cDNA encoding mammaglobin packaged in a container. The two primers have nucleotide sequences comprising SEQ ID NO:3 and SEQ ID NO:4.

In another embodiment of the present invention, the presence of mammaglobin protein expressed by a tumor cell is detected in a sample using specific antibodies to the mammaglobin protein. The specific antibodies can be polyclonal or monoclonal antibodies.

The invention is also directed to novel compositions and methods for treating breast neoplastic disease using mammaglobin antigens capable of inducing an antibody-mediated and/or a cell-mediated, i.e., through activated T cells, immune response against a mammaglobin-expressing tumor.

One embodiment of a composition according to the invention comprises a mammaglobin B cell antigen capable of activating mammaglobin-specific B cells. The B cell antigen comprises a mammaglobin-specific B cell epitope and a $T_H$ epitope, or determinant, recognized by T helper cells.

In another embodiment, the mammaglobin antigen is a mammaglobin $T_C$ cell antigen recognized by mammaglobin-specific cytotoxic T lymphocytes which comprises a $T_C$ cell epitope and a binding site, or agretope, for a MHC class I molecule.

Yet another embodiment of a composition according to the invention comprises B cell and $T_C$ cell antigens.

Methods for treating a patient with a mammaglobin-expressing tumor include adoptive immunotherapy, which comprises ex vivo stimulation with a mammaglobin antigen of mammaglobin-specific lymphocytes isolated from the patient and subsequent administration of the activated lymphocytes to the patient, and in vivo stimulation of an anti-mammaglobin immune response, which comprises administering to the patient a vaccine comprising a mammaglobin antigen.

Among the several advantages found to be achieved by the present invention, therefore, may be noted the provision of a nucleotide sequence and encoded amino acid sequence that can serve as markers for breast cancer cells; the provision of methods for early detection of the presence of breast neoplasia cells; the provision of means for detecting breast cancer that can complement mammography and increase the predictive value; the provision of methods that can provide an estimation of prognosis; the provision of markers that will allow the targeting of therapy; and the provision of compositions for stimulating a cellular and humoral immune response against the tumor.

BRIEF DESCRIPTION OF THE DRAWINGS

FIG. 2 illustrates the human cDNA sequence of SEQ ID NO:1 (nucleotides numbered above) and the amino acid sequence of the encoded mammary-specific protein, mammaglobin (SEQ ID NO:2)(amino acids numbered below), the solid bar indicating the 403 bp fragment (SEQ ID NO:5) isolated by the RACE PCR method and the open bar indicating the 206 bp DEST002 sequence (SEQ ID NO:6);

FIG. 3 illustrates the amino acid sequence of the mammary-specific protein, mammaglobin (hMAM), (SEQ ID NO:2) compared to rat prostatic steroid binding protein subunit C3 (rPSC3)(SEQ ID NO:7) and human clara cell 10 kD protein (hCC10)(SEQ ID NO:8) with identities marked by bold letters and double lines and structurally similar amino acids marked by single lines;

DESCRIPTION OF THE PREFERRED EMBODIMENTS

One aspect of the present invention is based upon the identification and sequencing of the cDNA identified as SEQ ID NO:1 which encodes a mammary-specific secretory protein, mammaglobin, identified by SEQ ID NO:2 (FIG. 2).

As described below, the full length mammaglobin cDNA was isolated starting from tumor cell mRNA that was reverse transcribed, amplified using the technique of PCR and subcloned into expression vectors. In addition, the protein, mammaglobin, encoded by the cDNA was identified and characterized.

Figure 1:
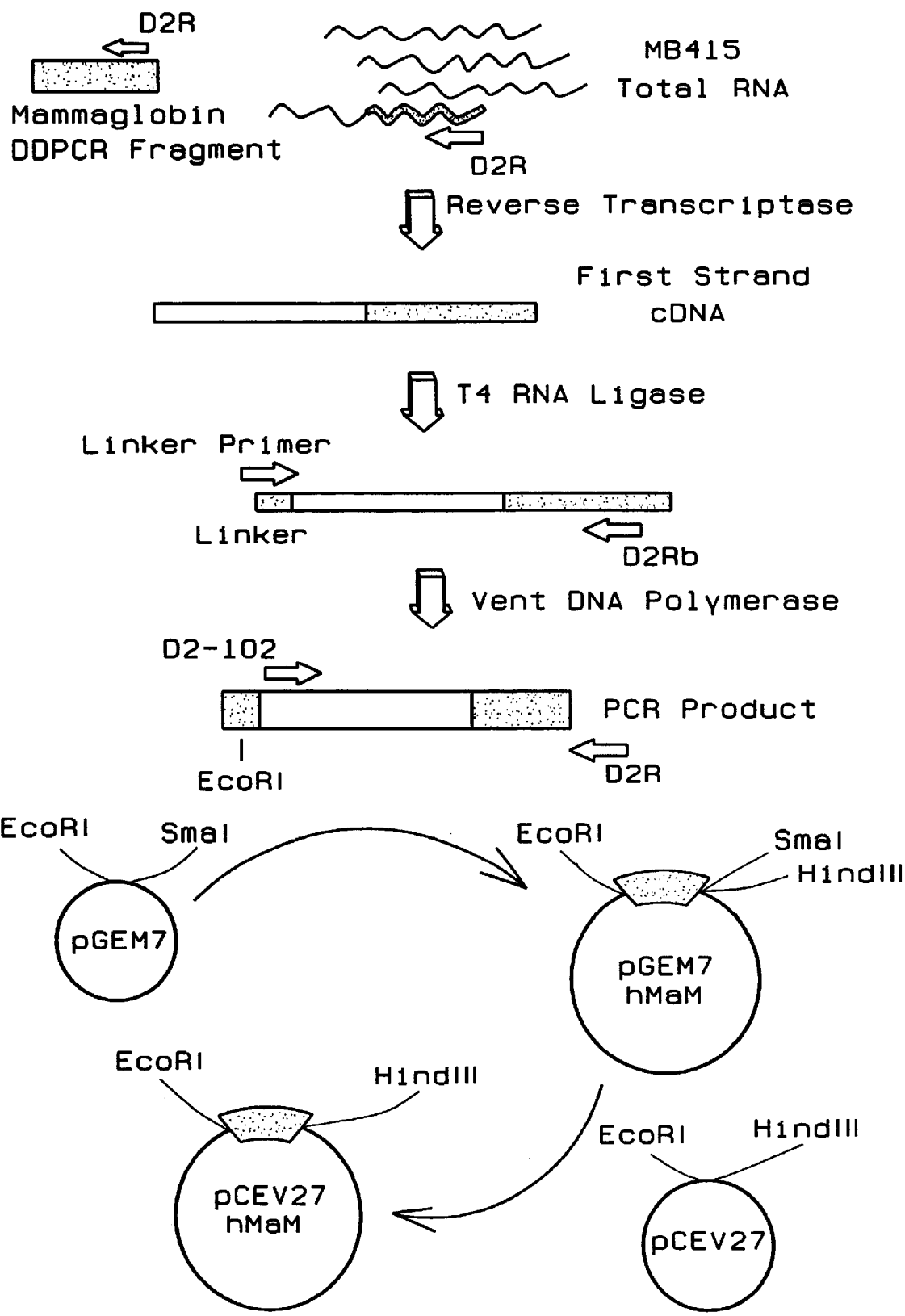
FIG. 1 illustrates the strategy used to isolate the full length mammaglobin cDNA including the Rapid amplification of cDNA Ends (RACE) Polymerase Chain Reaction (PCR) technique and subsequent subcloning into vectors pGEM7Z and pCEV27.

Using the anonymous sequence tag previously designated DEST002, it was demonstrated that the corresponding gene product, which was up until now unknown but herein identified as mammaglobin, is particularly abundant in the breast cancer tumor cell line MDA-MB-415. To isolate the full length mammaglobin cDNA, the mRNA was reverse transcribed from this cell line and cloned using the RACE PCR technique (Edwards et al. *Nucleic Acids Research* 19:5227–32, 1991 which is incorporated by reference). This technique is based upon the strategy of ligation of single-stranded oligodeoxyribonucleotide to the 3' end of single-stranded cDNA. The method by which the mammaglobin cDNA was isolated is represented schematically in FIG. 1.

The full length 503 bp cDNA sequence (SEQ ID NO:1) was deduced from the sequence information obtained from the 403 bp fragment (SEQ ID NO:5) (FIG. 2) isolated by this technique along with sequence information previously obtained from the corresponding DEST sequence (DEST002. SEQ ID NO:6) (FIG. 2) in our earlier study (Watson and Fleming, supra). Within the 503 bp cDNA is a 279 bp open reading frame which encodes a polypeptide of 93 amino acids and predicted molecular mass of 10.5 kD (SEQ ID NO:2) (FIG. 2). The initial methionine of this open reading frame is within a near-perfect Kozak consensus sequence (Kozak, *Cell* 22:7–8, 1980 which is incorporated by reference). The 60 bp upstream of this sequence contain no other in-frame methionines or translational stops. The 3' untranslated sequence of the cDNA constitutes 163 bp and contains a polyadenylation signal, AATAAA, 12 bp upstream of the priming site of the original DEST002 sequence. These data indicate that the full length mammaglobin cDNA has been isolated. The first 19 residues of the encoded polypetide predict a hydrophobic peptide signal sequence and residues 53–55 and 68–70 are consensus N-linked glycosylation sites, indicating that mammaglobin is a secreted glycoprotein.

A search for DNA sequences similar to the mammaglobin cDNA sequence in Genbank using the BLAST algorithm (Benson et al., *Nucl Acid Res* 21:2963–2965, 1993; Altschul et al, *J Mol Biol* 215:403–410, 1990 which are incorporated by reference), identified no obvious DNA sequence homologies. Thus, mammaglobin cDNA is believed to be a novel, heretofore unknown DNA sequence.

A search of other polypeptides for sequences related to mammaglobin revealed an amino acid sequence homology between mammaglobin and other polypeptides. Mammaglobin exhibited 42% amino acid identity (58% including conservative substitutions) with rat prostatic steroid binding protein (prostatein) subunit C3 (rPSC3) (FIG. 3) (SEQ ID NO:7). Rat prostatic steroid binding protein is a major secretory protein in the rat ventral prostate consisting of a tetrameric protein composed of two different dimeric subunits; C3/$C_1$ and C3/C2 (Parker et al., *Ann N Y Acad Sci* 438:115–124; Parker et al., *J Steroid Biochem* 20:67–71, 1984 which are incorporated by reference). The C1, C2, and C3 genes all encode approximately 6 kD secretory proteins and are thought to have arisen from gene duplication, but while the C1 and C2 genes show strong homology to each other, they are much less similar to the C3 gene. Correspondingly, mammaglobin shows no sequence homology with the C1 or C2 proteins.

As noted above, prostatic steroid binding protein (prostatein) is the major secretory protein in the rat ventral prostate and its expression is regulated by androgenic steroids (Parker et al, *Ann N Y Acad Sci* 438:115–24, 1984; Parker et al, *J Steroid Biochem* 20:67–71, 1984 which are incorporated by reference). Another protein, human estramustin-binding protein (hEMBP) has been reported to be expressed in human prostate, human breast cancer and human malignant melanoma. (Bjork et al, *Cancer Res* 42:1935–1942, 1982; Bjork et al, *Anticancer Res* 11:1173–82, 1991 which are incorporated by reference). Human estramustin-binding protein is immunochemically similar to rat estramustin-binding protein, which has been postulated to be identical to rat steroid-binding protein, prostatein. As noted above, the amino acid sequence of mammaglobin exhibited 42% amino acid identity and 58% homology including conservative substitutions with the C3 subunit of prostatein. Thus it is possible that mammaglobin could be in some way related to hEMBP. However, while both prostatein and hEMBP are detected in the prostate gland, mammaglobin mRNA is completely absent in this tissue. Hence, mammaglobin is neither the same protein nor a subunit of hEMBP and, furthermore, the sequence of hEMBP has not been determined so that it is not known whether there is even any similarity of mammaglobin with some fragment or subunit of hEMBP.

Although recent reports have demonstrated the rPSC3 promoter fused to SV40 T antigen produces both prostatic and mammary carcinomas in transgenic mice (Maroulakou et al., *Proc Nat Acad Sci U.S.* 91:11236–11240, 1994; Sandmoller et al, *Oncogene* 9:2805–2815, 1994 which are incorporated by reference), the true biological function of this protein is unknown. Furthermore, notwithstanding the hypothesized relationship of rat prostatic steroid binding protein to human EMBP, no human polypeptide or human gene corresponding to rPSC3 has been identified. Thus, mammaglobin and the cDNA encoding mammaglobin represent novel sequences heretofore unknown.

Using manual alignment with other sequences that had less significant BLAST scores with both mammaglobin and rPSC3 protein sequences, we identified other homologies with human clara cell 10 kD protein (hCC10) (SEQ ID NO:8) (Peri et al, *J Clin Invest* 92:2099–2109, 1993 which is incorporated by reference) (FIG. 3) and, in addition, with rabbit and mouse uteroglobin proteins (Miele et al., *Endocrine Rev* 8:474–90, 1987; Cato and Beato, *Anticancer Res* 5:65–72, 1985: Miele et al., *J Endocrinol Invest* 17:679–692, 1994 which are incorporated by reference). These homologies, depending on species, were 26% identity or 40% including conservative substitutions. In particular, a number of amino acids were perfectly conserved among all proteins, including Cys-3 and Cys-69 which are known to play a role in disulfide bond formation between uteroglobin subunits (see below). These homologies suggest that mammaglobin is a novel member of a small family of proteins that are secreted by epithelial cells (Miele et al, 1994, supra).

The hCC10 gene is the human homologue of rabbit and mouse uteroglobin genes (Peri et al, *J Clin Invest* 92:2099–2109, 1993 which is incorporated by reference). Uteroglobin was originally characterized as a secretory protein in rabbit uterus, but has since been found in other epithelial organs including lung, breast and prostate. Unlike rat prostatein, uteroglobin is a homodimeric protein coupled by two disulfide linkages at the conserved residues Cys-2 and Cys-69 (Miele et al, 1994, supra). Although uteroglobin gene transcription is regulated by steroid hormones, the ability of the protein itself to bind progesterone or other steroid hormones is controversial and again, the true biological function of this protein is unknown (Miele et al., 1994, supra).

Mammaglobin expression is restricted to the mammary gland. This is in contrast to the observation that rPSC3 is expressed in rat ventral prostate (Parker et al., *Ann N Y Acad Sci* 438:115–1124, 1984), and the expression of hCC10/uteroglobin in numerous tissues including lung, uterus, prostate, and breast (Miele et al., 1987, supra; Cato and Beato, supra; Miele et al., 1994 supra). Because of the sequence homology between mammaglobin and these proteins, we determined the pattern of tissue specific expression.

Figure 4A:
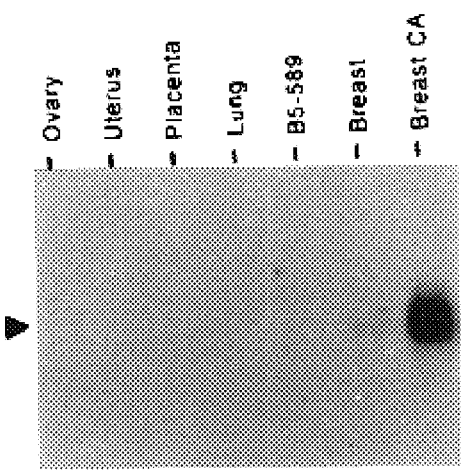
FIG. 4 illustrates (A) the Northern blot analysis of hybridization of the human cDNA sequence encoding the mammary-specific protein, mammaglobin (hMAM), to mRNA expressed by tissues from breast neoplasia, normal breast and other adult tissues and (B) the analysis of RT/PCR amplified samples of tissues from breast neoplasia, normal breast and other adult tissues.

The 500 bp mammaglobin mRNA was easily detected in tumor specimen 2410 (the tissue from which this original sequence tag was isolated) and to a much less extent in normal human breast tissue (FIG. 4A). Mammaglobin mRNA could not be detected in the immortalized breast epithelial cell line B5–589. Expression of mammaglobin was also undetectable in human uterus and lung, two sites of uteroglobin expression.

Figure 4B:
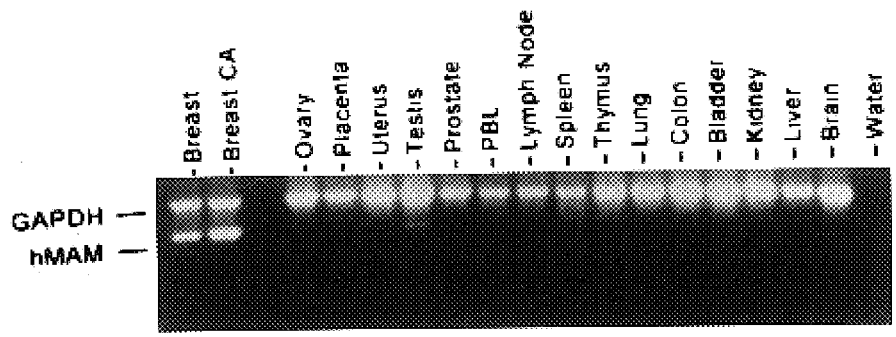

Amplification using RT/PCR detected mammaglobin mRNA in both tumor 2410 and normal breast tissue, but not in 15 other tissues surveyed, including tissues that normally express rPSC3 and uteroglobin (lung, uterus, prostate), hormonally responsive and steroidogenic tissues (ovary, testis, placenta), and other secretory epithelial organs (colon) (FIG. 4B). Therefore, the expression of mammaglobin mRNA is relatively specific for mammary tissue.

Based on the studies in this report, mammaglobin is a relatively mammary-specific protein. Two other genes known to be overexpressed in breast carcinoma are erb-B and cyclin D (Jardines et al, *Pathobiology* 61:268–282, 1994; Keyomars and Pardee, *Proc Nat Acad Sci U.S.* 90:1112–1116, 1993 which is incorporated by reference). Unlike the overexpression of erb-B or cyclin D, the overexpression of mammaglobin may reflect a more specific alteration of the mammary epithelial cell rather than a general increased growth potential or mitotic rate. As such, appearance of mammaglobin gene dysregulation may have more specific import for the therapeutic vulnerability or clinical course of a tumor.

Mammaglobin expression could not be detected in normal lymph nodes or peripheral lymphocytes at the level of sensitivity afforded by a single step RT/PCR assay. This suggests that analysis of mammaglobin transcripts in peripheral lymph nodes may be useful for detecting occult breast cancer metastases, as has been suggested for other epithelial specific genes (Schoenfeld et al., *Cancer Res* 54:2986–90 which is incorporated by reference).

Figure 5:
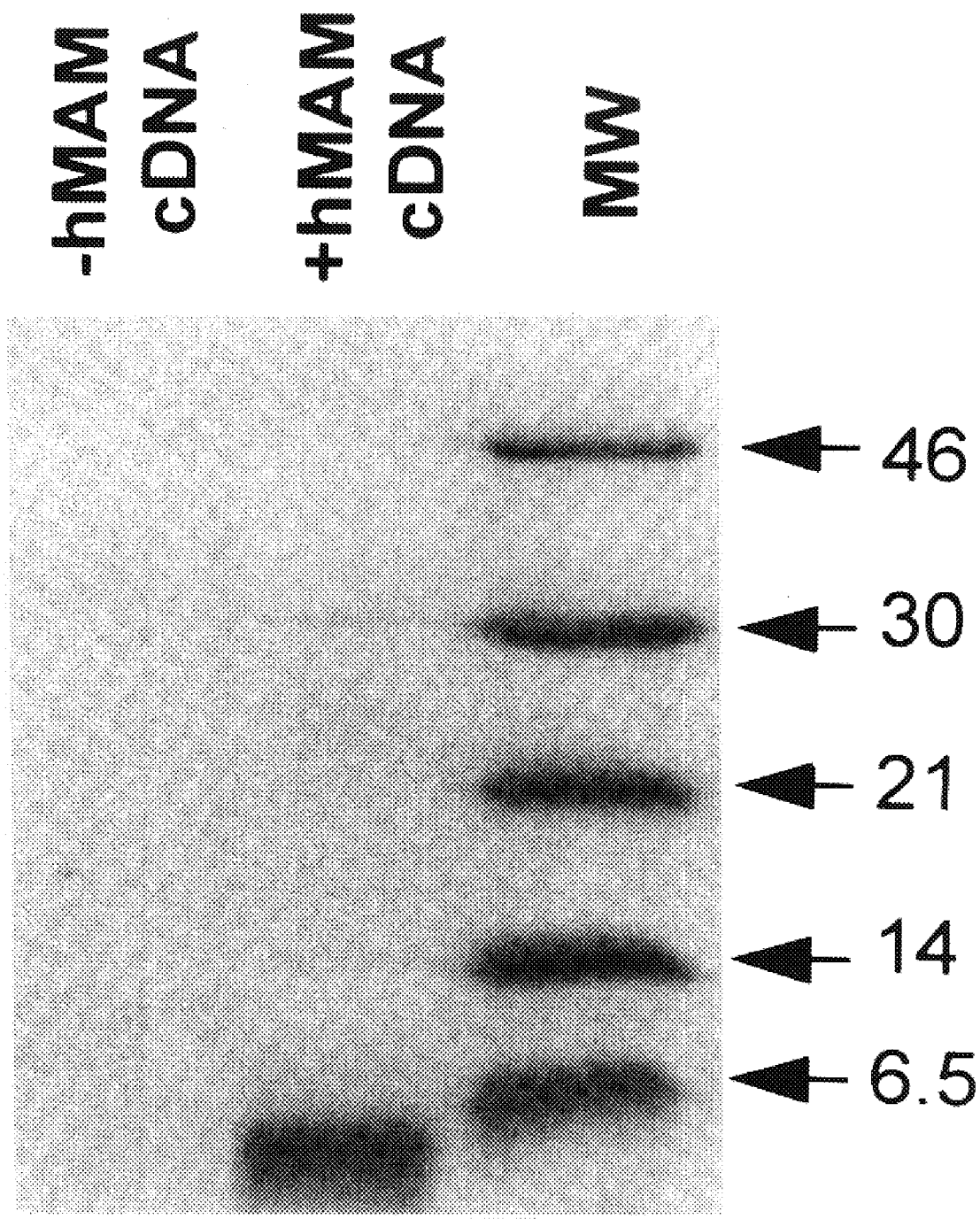
FIG. 5 illustrates the translation of the mammary-specific cDNA sequence in an in vitro rabbit reticulocyte lysate assay system.

To demonstrate that the mammaglobin cDNA encoded a translatable protein, the cDNA clone was used in an in vitro translation assay. FIG. 5 shows the protein product from a rabbit reticulocyte lysate programmed with the mammaglobin cDNA. An approximately 6 kD protein is generated using the mammaglobin cDNA. The apparent molecular weight is smaller than that predicted from conceptual translation of the open reading frame, but this finding is commonly observed with rabbit and human uteroglobin translation products as well.

Figure 6:
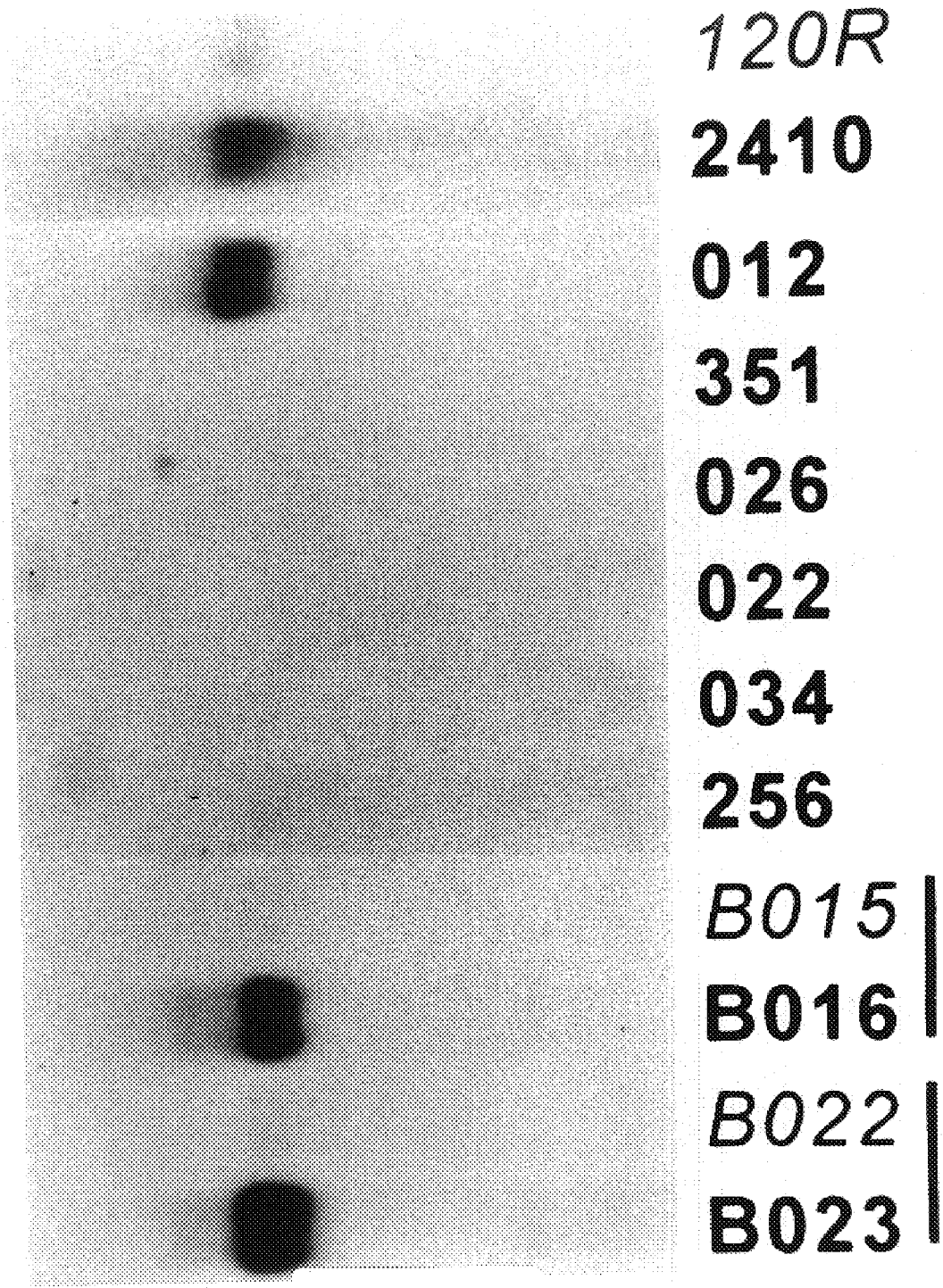
FIG. 6 illustrates Northern blot hybridization with the cDNA encoding mammaglobin showing detection of mRNA in tumor 2410, in tumors from three of eight other patients (shown in bold), and to a lesser extent, in normal breast tissue (shown in italics), and comparing in two cases (the four lanes on the right) mammaglobin mRNA expression in tumor tissue and patient matched normal tissue.

Although we detected overexpression of mammaglobin RNA in one tumor specimen (i.e. 2410), it was not clear at what frequency this overexpression is seen in other breast carcinomas. We therefore examined a panel of fifteen, stage I primary breast carcinomas of differing histological types by Northern blot hybridization with the mammaglobin cDNA probe. Because of potential variability in expression due to environment influences (e.g. patient hormonal status), we also sought to compare tumor specimens directly with patient-matched normal breast tissues samples, although this was not possible in many cases. As shown in FIG. 6, the 500 bp mammaglobin mRNA was again detected in normal breast tissue and tumor 2410. Mammaglobin was also detected in three other tumors, two of which demonstrated little or no expression in patient-matched normal tissue (BO15 and BO22). In all, 4 of 15 (27%) of tumors examined overexpressed mammaglobin mRNA. These data suggest that overexpression of mammaglobin is not unique to a single tumor specimen and is, in fact, relatively frequent among primary breast tumors. Furthermore, the fact that all tumors examined were stage I suggests that this dysregulation occurs relatively early in the progression of breast neoplasia.

Because Applicants believe mammaglobin is a secreted protein, its presence would be expected to be detectable in sera from patients whose tumors overexpress this gene product. As such, mammaglobin is likely to be as clinically useful as prostate specific antigen (PSA) and other solid tumor markers for managing patients with breast cancer (Tumor markers in diagnostic pathology, *Clin Lab Med* 10:1–250, 1990 which is incorporated by reference).

We determined the prevalence of mammaglobin as a tumor marker in the general population of breast cancer tumors by examining the expression of mammaglobin in several primary breast carcinomas. Although the number of specimens examined in this study was small, 27% of tumors evaluated overexpressed mammaglobin mRNA. This percentage is comparable to the prevalence of other genetic alterations such as erb-B amplification and p53 mutation (Slamon et al. *Sci* 244:707–712, 1989; Thor et al, *J Nat'l Cancer Inst* 84:845–855, 1992 which are incorporated by reference). Furthermore, because we have restricted our analysis to stage I tumors, overexpression of mammaglobin would actually be more prevalent than any other genetic alteration reported in this subgroup of tumors (Alllerd et al, *J Nat'l Cancer Inst* 85:200–206, 1993 which is incorporated by reference).

The identification of mammaglobin as a breast cancer marker provides the basis for another aspect of the present invention, which involves methods for detecting the presence of breast cancer in a patient. The term "detection" as used herein in the context of detection of breast neoplastic disease is intended to be a comprising aspect of the determining of the presence of breast cancer in a patient, the distinguishing of breast cancer from other diseases, the estimation of prognosis in terms of probable outcome of the disease and prospect for recovery, the monitoring of the disease status or the recurrence of the disease, the determining of a preferred therapeutic regimen for the patient and the targeting of antitumor therapy.

A method for detecting breast cancer comprises hybridizing a polynucleotide to mRNA from breast neoplasia cells. The polynucleotide comprises SEQ ID NO:1 or a derivative of SEQ ID NO:1. A derivative of a nucleotide sequence means that the derived nucleotide sequence is substantially the same as the sequence from which it is derived in that the derived nucleotide sequence has sufficient sequence complementarity to the sequence from which it is derived to hybridize to mRNA from breast neoplasia cells under the same stringency conditions that the sequence from which it is derived hybridizes to the mRNA from breast neoplasia cells. The derived nucleotide sequence is not necessarily physically derived from the nucleotide sequence, but may be generated in any manner including for example, chemical synthesis or DNA replication or reverse transcription or transcription.

To detect the presence of mRNA encoding mammaglobin in a detection system for breast cancer, a sample is obtained from a patient. The sample can be a tissue biopsy sample or a sample of blood, plasma, serum or the like. The sample may be treated to extract the nucleic acids contained therein. The resulting nucleic acid from the sample is subjected to gel electrophoresis or other size separation techniques.

Detection involves contacting the nucleic acids and in particular the mRNA of the sample with a DNA sequence serving as a probe to form hybrid duplexes. The term "probe" refers to a structure comprised of a polynucleotide which forms a hybrid structure with a target sequence, due to complementarily of probe sequence with a sequence in the target region.

Detection of the resulting duplex is usually accomplished by the use of labeled probes. Alternatively, the probe may be unlabeled, but may be detectable by specific binding with a ligand which is labeled, either directly or indirectly. Suitable labels and methods for labeling probes and ligands are known in the art, and include, for example, radioactive labels which may be incorporated by known methods (e.g., nick translation or kinasing), biotin, fluorescent groups, chemiluminescent groups (e.g., dioxetanes, particularly triggered dioxetanes), enzymes, antibodies, and the like.

When using the cDNA encoding mammaloglobin or a derivative thereof as a probe, high stringency conditions can be used in order to prevent false positives. When using sequences derived from mammaglobin, less stringent conditions can be used. The stringency of hybridization is determined by a number of factors during hybridization and during the washing procedure, including temperature, ionic strength, length of time and concentration of formamide. These factors are outlined in, for example, Sambrook et al. (*Molecular Cloning: A Laboratory Manual,* 2d ed., 1989).

In order to increase the sensitivity of detection of mammaglobin mRNA in a sample, the technique of reverse transcription/polymerization chain reaction (RT/PCR) can be used to amplify cDNA transcribed from mRNA encoding mammaglobin. The method of RT/PCR is well known in the art (for example, see Watson and Fleming, supra).

The RT/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and mammaglobin specific primers. (Belyavsky et al, *Nucl Acid Res* 17:2919–2932, 1989, Krug and Berger, *Methods in Enzymology,* Academic Press. N.Y., Vol. 152, pp. 316–325, 1987 which are incorporated by reference)

The polymerase chain reaction method is performed using two oligonucleotide primers that are complementary to the two flanking regions of the DNA segment to be amplified. The upstream and down stream primers are typically from 20 to 30 base pairs in length and hybridize to the flanking regions for replication of the nucleotide sequence. The primers are selected to be substantially complementary to the strand of cDNA being amplified. Therefore, the primers need not reflect the exact sequence of the template, but must be sufficiently complementary to selectively hybridize with the strand being amplified.

Polymerization from the primers is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, the method of physical denaturation is used involving heating the nucleic acid, typically to temperatures from about 80° C. to 105° C. for times ranging from about 1 to 10 minutes. The process is repeated for the desired number of cycles.

Following amplification, the PCR product is then detected by ethidium bromide staining (Sambrook, et al., 1989, supra).

In another embodiment of the present invention, the mammaglobin cDNA sequence or derivative thereof can be used to characterize any alteration of the mammaglobin gene (i.e. gene rearrangement, gene amplification, or gene deletion) in a specimen from a breast-cancer patient. This provides a method whereby patient specimens or samples, which do not contain intact mRNA, can still be examined for changes in gene structure.

In one application of this technique, the mammaglobin cDNA sequence or derivative thereof is hybridized to patient genomic DNA that has been isolated from a patient's tumor, normal tissue, or lymphocytes and digested with one or more restriction endonucleases. Using the Southern blot protocol, which is well known in the art, this assay determines whether a patient or a patient's breast tumor has a mammaglobin gene, which was deleted, rearranged, or amplified. Detection of these changes can then provide important information useful for predicting prognosis and for patient management.

In a second application of this technique, one or more pairs of oligonucleotide primers based on the mammaglobin cDNA sequence or derivative thereof could be used in the polymerase chain reaction to amplify segments of the mammaglobin gene from a patient sample. Analysis of the resulting PCR products indicate whether a particular segment of the mammaglobin gene is deleted or rearranged. Such information is useful for prognosis and patient management.

Another method for detecting breast cancer comprises detecting the presence of the precursor and/or secreted forms of the mammaglobin polypeptide in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see *Basic and Clinical Immunology,* Sites and Terr, eds., Appleton & Lange, Norwalk, Conn. pp 217–262, 1991 which is incorporated by reference). Preferred are binder-ligand immunoassay methods including reacting antibodies with an epitope or epitopes of mammaglobin and competitively displacing a labeled mammaglobin polypeptide or derivative thereof.

As used herein, the term "mammaglobin polypeptide" embraces naturally occurring mammaglobin, including non-glycosylated and glycosylated precursor forms and the glycosylated secreted form, derivatives and fragments thereof. By naturally occurring is meant a polypeptide that can be isolated from a source in nature, e.g., from normal and/or diseased organisms, and that has not been intentionally modified by man.

A derivative of mammaglobin is intended to refer to polypeptides which are comprised of a segment of at least 10 amino acids that has substantial identity to a portion of naturally occurring mammaglobin. The segment having substantial identity is preferably at least about 20 amino acids, more preferably at least about 50 amino acids, and most preferably at least about 75 amino acids. Two polypeptides have substantial identity when upon optimal alignment by sequence alignment programs such as BLAST, they share at least 80 percent sequence identity, preferably at least 95 percent sequence identity, more preferably at least 95 percent sequence identity, most preferably 99 percent sequence identity. Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups are: valine-leucine-isoleucine, phenylalanine-tyrosine, lysine-arginine, alanine-valine, and asparagine-glutamine.

A derivative mammaglobin polypeptide will preferably cross-react with an anti-mammaglobin antibody, monoclonal or polyclonal, which is specific for naturally occurring mammaglobin or fragments thereof.

As used herein the terms "fragment" and "peptide" refer to a mammaglobin polypeptide having an amino acid sequence identical to the amino acid sequence deduced from a full-length mammaglobin cDNA (e.g., SEQ ID NO:1) or derivative thereof, but that has an amino-terminal and/or carboxy-terminal deletion. Typically, mammaglobin fragments or peptides are at least 3 amino acids long. Preferably a mammaglobin fragment or peptide is at least 6 amino acid residues in length, more preferably about 12 amino acid residues in length, even more preferably about 25 amino acid residues in length, and most preferably 50 amino acid residues or greater.

Numerous competitive and non-competitive protein binding immunoassays are well known in the art. Antibodies employed in such assays may be unlabeled, for example as used in agglutination tests, or labeled for use a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to a mammaglobin polypeptide comprising a B cell epitope can be made for use in immunoassays by any of a number of methods known in the art. As used herein, the term "B cell epitope" refers to an antigenic determinant of a mammaglobin polypeptide. A B cell epitope could comprise 3 amino acids in a spacial conformation which is unique to the epitope. Generally, a B cell epitope consists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse.

Methods for preparation of a mammaglobin polypeptide include, but are not limited to chemical synthesis, recombinant DNA techniques or isolation from biological samples. Chemical synthesis of a peptide comprising an epitope can be performed, for example, by the classical Merrifeld method of solid phase peptide synthesis (Merrifeld, *J Am Chem Soc* 85:2149, 1963 which is incorporated by reference) or the FMOC strategy on a Rapid Automated Multiple Peptide Synthesis system (DuPont Company, Wilmington, Del.) (Caprino and Han, *J Org Chem* 37:3404, 1972 which is incorporated by reference).

Polyclonal antibodies can be prepared by immunizing rabbits by injecting antigen into the popliteal lymph nodes followed by subsequent boosts at two week intervals with intraperitoneal injection of antigen. The animals are bled and sera assayed against purified mammaglobin protein, usually by ELISA.

Monoclonal antibodies can be prepared after the method of Milstein and Kohler by fusing splenocytes from immunized mice with continuously replicating tumor cells such as myeloma or lymphoma cells. (Milstein and Kohler Nature 256:495–497, 1975; Gulfre and Milstein, *Methods in Enzymology: Immunochemical Techniques* 73:1–46, Langone and Banatis eds., Academic Press, 1981 which are incorporated by reference). The hybridoma cells so formed are then cloned by limiting dilution methods and supernates assayed for antibody production by ELISA or RIA.

Thus prepared polyclonal or monoclonal antibodies to mammaglobin may be used to isolate and purify precursor and secreted forms of mammaglobin from cells expressing mammaglobin. For example, as shown below, a polyclonal antibody generated against the 16 C-terminal amino acids predicted from mammaglobin cDNA (Glu-Val-Phe-Met-Gln-Leu-Ile-Tyr-Asp-Ser-Ser-Leu-Cys-Asp-Leu-Phe, SEQ ID NO:14) binds to precursor and secreted forms of mammaglobin, as well as to mammaglobin that has been synthesized in an in vitro translation system. Isolation of mammaglobin using an anti-mammaglobin antibody may be accomplished using procedures well-known in the art, such as affinity chromatography.

The unique ability of antibodies to recognize and specifically bind to target antigens expressed by a tumor cell provides an approach for the treatment of cancer. (For review see LoBuglio and Saleh, *Am J Med Sci* 304:214–224, 1992; Bagshawe, *Adv Pharmacol* 24:99–121, 1993 which are incorporated by reference). Thus, another aspect of the present invention provides for a method for preventing the onset and treating breast cancer in an animal based upon the use of antibodies to mammaglobin, which has been discovered to be overexpressed by breast cancer cells.

Specific antibodies to mammaglobin, either polyclonal or monoclonal, are produced by any method known in the art. For example, murine or human monoclonal antibodies can be produced by hybridoma technology. Alternatively, mammaglobin, or an immunologically active derivative or fragment thereof, or an anti-idiotypic antibody, or fragment thereof, can be administered to an animal to elicit B cell production of antibodies capable of recognizing the mammaglobin-expressing cells.

The antibodies so produced or fragments thereof are labeled with one or more oncolytic substances such as radionuclides, toxins, or cytotoxic drugs and administered to a patient suspected of having breast cancer. The binding of the labeled antibody to the mammaglobin being overexpressed by the breast cancer cell will cause the death of the cancer cell.

Any of a variety of oncolytic substances known in the art can be used to produce such labeled antibodies. For example, immunotoxins can be made by coupling plant and bacterial toxins to antibodies. Such toxins include, for example, ricin, diphtheria toxin and Pseudomonas exotoxin A. Drug-antibody conjugates can also be made in which chemotherapeutic agents are linked to the antibody. Chemotherapeutic agents suitable for such use include, for example, tomoxifen, doxorubicin, methotrexate, chlorambucil, Vinca alkaloids, and mitomycin. In addition, radioimmunoconjugates can be made in which a radionuclide is stably linked to the antibody. Radionuclides suitable for making radioimmunoconjugates include, for example, β-emmitters such as $^{131}$I, $^{188}$Re, $^{186}$Re, $^{67}$Cu, $^{90}$Y and $^{47}$Sc; α-emitters such as $^{211}$At, $^{212}$Bi and $^{212}$Pb; auger electron emitters such as $^{125}$I and $^{77}$Br; and fissionable nuclides such as $^{10}$B.

The finding that a significant percentage of breast tumors express mammaglobin protein is the basis for another aspect of the invention, which involves the activation of mammaglobin-specific B and/or T cell lymphocytes ($T_C$) with mammaglobin antigens. Accordingly, the invention provides mammaglobin B cell antigens and $T_C$ cell antigens; vaccines comprising at least one B cell mammaglobin antigen and/or at least one $T_C$ mammaglobin antigen for inducing antibody- and/or cell-mediated immune responses against mammaglobin-expressing tumors, and methods for treating a breast cancer patient with a mammaglobin-expressing tumor. One method according to the invention comprises administering to the patient activated mammaglobin-specific lymphocytes. Another method comprises administering to the patient a mammaglobin-specific vaccine.

As used herein, "mammaglobin antigen" includes naturally occurring mammaglobin polypeptides, derivatives, and fragments thereof which contain a B cell or $T_C$ cell epitope recognized by mammaglobin-specific B cells or $T_C$ cells.

A mammaglobin B cell antigen comprises a mammaglobin-specific B cell epitope and a $T_C$ cell epitope. The term "B-cell epitope" refers to any antigen, hapten, epitope or antigenic determinant which is recognized by anti-mammaglobin immunoglobulin receptors on B cells and is capable of eliciting the production of antibodies with appropriate help from $T_H$ cells when administered to an animal. The B cell epitope comprises an amino acid sequence of at least 4 amino acids. Preferably, the B cell epitope is between at least 6 and 25 amino acids in length and more preferably is between about 15 and 22 amino acids in length. The comprising amino acid sequence of the B cell epitope may be identical or substantially identical to a continuous amino acid sequence in a fragment of naturally occurring mammaglobin. Alternatively, the comprising amino acid sequence of a B cell epitope is identical to or substantially identical to a discontinuous amino acid sequence representing an assembled topographic determinant of mammaglobin.

The term "$T_H$ cell epitope" refers to any antigenic determinant recognized by T helper cells through association with MHC class II molecules. The activation of T helper cells induces differentiation of resting mammaglobin-specific B cells into higher affinity IgG-secreting cells, i.e, induces a secondary antibody response. The preparation and use of immunogenic peptides containing B and $T_H$ cell determinants to produce higher titres of specific antibody-producing B cells through T cell help is known in the art, see, e.g., Cheronis et la., U.S. Pat. No. 5,573,916, Denton, et la., *Cancer Letters* 70:143–150 (1993), Borras-Cuesta et al., *Eur. J. Immunol.* 17, 1213–1215 (1987), and Good et al., *Science* 235:1059–1062 (1987), each of which is incorporated herein by reference. The $T_H$ cell epitope may comprise an amino acid sequence from mammaglobin or a heterologous protein. For example, Denton et al. describe the induction of antibody responses to mucins, which are complex glycoproteins expressed in secretory epithelia and associated with breast and other carcinomas, in mice immunized with a synthetic peptide containing a B cell determinant region from the core of MUC-1 mucin linked to sequence 111–120 of influenza haemagglutinin A/X-31, a known helper T cell-determinant. The $T_H$ cell epitope comprises an amino acid sequence of between about 6 to about 20 amino acid residues, preferably between about 8 residues and 18 residues, even more preferably between 9 residues and 15 residues.

A mammaglobin $T_C$ cell antigen comprises a $T_C$ cell epitope and a MHC class I agretope. The term "$T_C$ cell epitope" means any antigen, epitope or antigenic determinant which is recognized by mammaglobin-specific $T_C$ cells when presented by a MHC class I molecule on the surface of an antigen presenting cell. The term "MHC class I agretope" refers to any amino acid sequence recognized by a MHC class I molecule that allows the mammaglobin antigen to be presented to a mammaglobin-specific $T_C$ cell by the MHC class I molecule on an antigen presenting cell (APC). The $T_C$ cell epitope and MHC class I agretope are contained within an amino acid sequence of between about 6 to about 11 amino acids that is identical or substantially identical to the amino acid sequence of a fragment of naturally occurring mammaglobin. Preferably, the sequence is 8 or 9 amino acids in length.

Methods for identifying B and $T_C$ cell epitopes for a protein antigen are known in the art. For example, the capacity of isolated mammaglobin-specific B cells or mammaglobin-specific $T_C$ cells to respond to overlapping synthetic peptides spanning secreted mammaglobin may be determined using standard immunobiology techniques. Those peptides identified as antigenic may then be modified one or a few amino acids at a time to optimize their ability to stimulate mammaglobin-specific B or T cells.

B cell epitopes can also be mapped using commercially available epitope mapping kits which involve the screening of random peptides bound at the C terminus to polyethylene multipin supports, e.g., Cambridge Research Biochemicals.

Alternatively, the predicted mammaglobin amino acid sequence may be searched for sequences that conform to known binding motifs of MHC class I or MHC class II molecules. See e.g, Hill et al., *Nature* 360:434 (1992), Pamer et al., *Nature* 360:852 (1992) and Hammer et al., *J. Exp. Med.* 176:1007 (1992), and Falk et al., *Nature* 351:290–296 (1991), each of which is herein incorporated by reference. For example, antigenic peptides recognizable by breast tumor-specific CTLs may be identified by searching the mammaglobin amino acid sequence for HLA-A2-binding peptides as described by Peoples et al., *Proc. Natl. Acad. Sci.* 92:432–436 (1995), which is incorporated herein by reference. The choice of HLA-A2 as the antigen presenting molecule is appropriate where the patient expresses HLA-A2 (approximately 50% of Caucasians express HLA-A2). The predicted HLA-A2 binding peptides can be synthesized and tested for antigenicity by loading the synthetic peptides onto the T2 cell line, a human T-cell/B-cell fusion product containing a defect in antigen presentation such that HLA-A2 molecules on the surface of T2 cells can be effectively loaded with exogenous HLA-A2 binding peptides (Henderson, et al, *Science* 255:1264–1266 (1992) incorporated herein by reference). A standard cytotoxicity assay is then carried out which comprises incubating the peptide-loaded T2 cells with breast-specific CTLs derived from tumor infiltrating lymphocytes (TILs) isolated from a mammaglobin-expressing breast tumor, e.g., see Peoples et al., pages 432–433 and Toso et al., *Cancer Research* 56:16–20 (1996), herein incorporated by reference.

Antigenic mammaglobin peptides containing $T_C$ cell epitopes may also be identified by acid-eluting endogenous peptides presented by HLA class I molecules on the tumor cell surface. (See, e.g., Peoples et al., supra, p. 433). The eluted peptides may be separated by any number of techniques known in the art, including HPLC fractionation. The different peptide fractions are loaded onto T2 cells and the loaded T2 cells are incubated with breast-tumor specific CTLs to determine which peptides are recognized by the CTLs using standard immunobiology techniques.

One use of a mammaglobin antigen according to the invention is in adoptive immunotherapy. This therapy involves in vitro activation and expansion by a mammaglobin antigen of anti-mammaglobin antibody-producing B cells and/or mammaglobin-specific cytotoxic T lymphocytes (CTLs) isolated from a patient with a mammaglobin-expressing tumor. The method may also be practiced with a composition comprising both mammaglobin B cell and $T_C$ cell antigens. The activated lymphocytes are then introduced back into the patient for adoptive immunotherapy.

A mammaglobin antigen according to the invention is also useful as a component of a mammaglobin-specific vaccine. The vaccine comprises an immunogenically-stimulatory amount of a mammaglobin antigen. As used herein, an immunostimulatory amount refers to that amount of antigen that is able to stimulate the desired immune response in the recipient for the amelioration, or treatment, of breast cancer. This amount may be determined empirically by standard procedures, well known to those of ordinary skill in the art, without undue experimentation.

The antigen may be provided in any one of a number of vaccine formulations which are designed to induce the desired type of immune response, e.g., antibody and/or cell mediated. Such formulations are known in the art. See, e.g., A. Lanzavecchia, *Science* 260:937–944 (1993) and U.S. Pat. No. 5,585,103 to Raychandhuri, each of which is incorporated herein by reference. Examples of vaccine formulations used to stimulate immune responses include pharmaceutically acceptable adjuvants such as aluminum salts; emulsions of squalene or squalane and muramyl dipeptide; liposomes; and a composition comprising a stabilizing detergent, a micelle-forming agent, and a biodegradable and biocompatible oil (Raychandhuri, supra).

A mammaglobin-specific vaccine may also comprise a carrier cell loaded with a mammaglobin antigen. Preferably, the carrier cell is prepared from autologous professional antigen presenting cells (APC) such as macrophages, dendritic cells, or activated B or T lymphocytes. See e.g., Lanzavecchia, supra, p. 937. Professional APCs express a ligand, B7, that binds to CD28 or CTLA4 on T cells to deliver an antigen-nonspecific costimulatory signal known as Signal 2 which prevents T cell anergy or inactivation. Thus, the vaccine may also comprise interleukin-2 or another costimulatory signal to counteract anergy induction. (Lanzavecchia, supra, p. 938.)

Another formulation of a mammaglobin-specific vaccine comprises a recombinant vector containing a nucleotide sequence encoding for expression a mammaglobin antigen. The use of infectious agents to stimulate cytotoxic T lymphocytes is known in the art. (Raychaudhuri, supra.) Chimeric vectors have been described using vaccinia, polio, adeno-and retro-viruses, as well as bacteria such as Listeria and BCG. For example, a canarypox virus vector, ALVAC, has been shown to elicit strong cellular immune responses against encoded heterologous gene products (Taylor et al, *Virology* 187:321–328 (1991), incorporated herein by reference). In addition, a recombinant ALVAC expressing the MZ2-E human melanoma rejection antigen encoded by the MAGE-1 gene is able to stimulate in vitro MAGE-1 CTL activities in a TIL population derived from a breast tumor expressing MAGE-1 mRNA (Toso et al, supra). In another approach described in U.S. Pat. No. 5,593,972 to Weiner et al (herein incorporated by reference), a recombinant expression vector encoding an antigen of an immunogenic protein to be targeted is directly administered to an individual either in vivo, e.g., to muscle cells, or to the cells of an individual ex vivo along with an agent that facilitates uptake of the DNA into the cells.

Those skilled in the art may readily determine how to formulate a vaccine suitable for achieving the desired immune response. For example, for inducing in vivo production of anti-mammaglobin antibodies, a mammaglobin-specific vaccine comprises at least one mammaglobin B cell antigen comprising a B cell epitope and a $T_H$ cell epitope. The $T_H$ cell epitope is preferably matched with the appropriate MHC class II haplotype of the intended vaccine recipient. Alternatively, a $T_H$ cell epitope could be used that is known to be recognized universally by humans regardless of HLA type such as the "universal" T cell epitope from tetanus toxoid (Panina-Bordignon et al. *Eur. J. Immunol.* 19:2237 (1989), herein incorporated by reference). Preferably, the vaccine comprises a plurality of mammaglobin B cell antigens with $T_H$ epitopes recognized by MHC Class H1 molecules of different HLA types.

Another embodiment of a mammaglobin-specific vaccine induces a cell-mediated response and comprises at least one mammaglobin $T_C$ antigen capable of activating mammaglobin-specific $T_C$ cells. Preferably, the vaccine comprises several $T_C$ cell antigens.

A mammaglobin-specific vaccine may also be formulated to induce both antibody and cell-mediated responses. This embodiment comprises both mammaglobin B cell and $T_C$ cell antigens.

A patient with a mammaglobin-expressing tumor may be treated by administering to the patient an immunostimulatory amount of a mammaglobin-specific vaccine according to the present invention. Administration of the vaccine may be by any known or standard technique. These include, but are not limited to intravenous, intraperitoneal, intramuscular, subcutaneous, or intramammary injection.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

In the examples below, cell lines were obtained from American Type Culture Collection and grown in Dulbecco's minimal essential medium supplemented with 10% fetal calf serum. Tissue biopsy specimens were obtained from the Human Cooperative Tissue Network (LiVolsi et al, *Cancer* 71:1391–1394, 1993 which is incorporated by reference).

EXAMPLE 1

This example illustrates the isolation of mammaglobin cDNA.

Total cellular RNA from the cell line MDA-MB415 was isolated using the standard guanidinium isothiocyanate method. (Belyavsky et al, supra). This RNA was used in the RACE PCR procedure employing the Amplifinder kit (Clonetech) and following the manufacturer's protocol.

The synthesis of first strand cDNA was performed in a standard reaction containing 1 μg RNA, 10 μM specific mammaglobin primer D2R (5'-ATA AGA AAG AGA AGG TGT GG-3')(SEQ ID NO:4), 4 μl of 5×RT buffer (250 mM TrisCl pH8.3, 375 mM Kcl, 15 mM MgCl$_2$), 2 μl of 100 MM DTT, 1 μl of 10 mM dNTPs and 200 units of Superscript™ II reverse transcriptase (Gibco/BRL) in a reaction volume 20 μl. The reaction proceeded for 1 hour at 45° C. and was terminated by incubating at 95° C. for 5 minutes. RNA was hydrolyzed with 400 μM NaOH at 65° C. for 30 minutes and neutralized with 400 μM acetic acid.

The reaction mixture was then added to 3 volumes of 6M NaI and 10 μl of treated glass beads. Beads were washed three times with 80% EtOH and nucleic acid was eluted from the beads in 45 μl of water. Nucleic acid was then precipitated and resuspended in 10 μl of water. The purified first strand cDNA was ligated to the manufacturer's provided anchor oligonucleotide (SEQ ID NO:9, 5'-CAC GAA TTC ACT ATC GAT TCT GGA ACC TTC AGA GG-3'), using T4 RNA ligase at 27° for 20 hours. One tenth of a ligation reaction was used for PCR amplification in a 50 μl reaction containing 1 μM manufacturer's anchor primer (SEQ ID NO:10, 5'-CTG GTT CGG CCC ACC TCT GAA GGT RCC AGA ATC GAT AG-3'), 1 μM mammaglobin specific primer D2Rb (SEQ ID NO:11, 5'-AAT CCG TAG TTG GTT TCT CAC C-3'), 200 μM dNTPs, 5 units of Vent™ DNA polymerase, and 1×polymerase buffer (10 mM Kcl, 20 mM TrisCl, 10 mM (NH$_4$)$_2$SO$_4$, 2 mM MgSO$_4$, 0.1% Triton X-100). The reaction was incubated at 94° for 2 minutes and then 94° for 45 seconds, 50° for 1 minute, and 72° for 90 seconds for a total of 40 times.

The two downstream mammaglobin-specific nested oligonucleotides were D2R (SEQ ID NO:4) and D2Rb (SEQ ID NO:11). An upstream mammaglobin-specific control oligonucleotide was also used as per the manufacturer's recommendations, D2F (5'-CTT TCT GCA AGA CCT TTG GC-3') (SEQ ID NO:12). All PCR amplifications were performed with Vent DNA polymerase (New England Biolabs). The amplified RACE product was digested with EcoRI and ligated into the EcoRI and SmaI sites of the plasmid vector pGEM7Z (Promega, Madison, Wis.).

All sequencing was performed using the Taq DNA polymerase thermal cycle sequencing kit as per the manufacture's protocol (Promega) Briefly the procedure used is as follows.

Ten pmol of sequence specific oligonucleotide was end labeled with 10 pmol of $^{32}$P-γ ATP (3,000 Ci/mmol and 10 mCi/ml) using T4 polynucleotide kinase in a 10 μl reaction for 30 minutes at 37° C. A polymerization reaction containing 100 ng of plasmid template, 1.5 pmol of labeled sequencing primer, and 5 units of sequencing grade Taq polymerase was created in 17 μl of the manufacturer's provided sequencing buffer. This reaction was aliquoted to a set of four reaction tubes containing manufacturer's provided mix of deoxynucleotides and either dideoxy-A, C, G, or T. The set of four tubes were incubated at 95° C. for 2 minutes and then, 94° C. for 45 seconds, 45° C. for 30 seconds, and 72° C. for 1 minute for 30 times. After reactions were completed, 3 μl of 80% formamide/bromphenol blue dye was added to each tube. Samples were heated to 70° C. for 2 minutes and loaded on a 6% acrylamide/7.5 M urea sequencing gel and run for 2–4 hours and 60 W constant power. The gel was dried and then exposed to Kodak XAR5 Xray film for 2 to 24 hours.

The sequence thus obtained was a 403 bp fragment (SEQ ID NO:5) as shown in FIG. 2, solid bar. In earlier work the DEST002 Tag sequence was isolated (Watson and Fleming, supra). This sequence was a 206 bp fragment (SEQ ID NO:6) as shown in FIG. 2, open bar. Combining the information from these two sequences allowed the full-length 503 bp cDNA of mammaglobin to be deduced. (FIG. 2).

EXAMPLE 2

This example demonstrates that mammaglobin expression is restricted to mammary gland tumor cells and, to a lesser extent, normal mammary gland cells.

Total cellular RNA samples were isolated using the standard guanidinium isothiocyanate method and treated with RNase-free DNase (Promega). For RT/PCR analysis, 1 μg of indicated total RNA was reverse transcribed with oligo dT$_{21}$, (SEQ ID NO:13) and Superscript II reverse transcriptase (Gibco/BRL) according to the manufacture's protocol.

Two hundred ng of oligo dT$_{21}$ (SEQ ID NO:13) and 1 μg of total RNA were incubated at 65° C. for 5 minutes in a 10 μl volume. Sample was chilled on ice and added to it were 4 μl of 5×RT buffer (250 nM TrisCl pH8.3, 375 mM Kcl, 15 mM MgCl$_2$), 2 μl of 100 mM DTT, 1 μl of 10 mM dNTPs and 200 units of Superscript™ II reverse transcriptase (Gibco/BRL). The reaction proceeded for 1 hour at 45° C. and was terminated by incubating at 95° C. for 5 minutes.

One tenth of each RT reaction was subject to PCR analysis using the mammaglobin specific primers D2R (5'-ATA AGA AAG AGA AGG TGT GG-3') (SEQ ID NO:4) and d2102 (5'-CAG CGG CTT CCT TGA TCC TTG-3') (SEQ ID NO:3) and standard reaction conditions for 40 cycles at 94°×30 sec./55°×1 min./72°×1 min.

For Northern analysis, 20 μg of total RNA was analyzed as previously described (Watson and Fleming, supra) using the full length mammaglobin cDNA probe. Integrity and equal loading of each RNA sample was assessed by ethidium bromide staining.

As shown in FIG. 4A, the 500 bp mammaglobin message is easily detected in tumor specimen 2410 (the tissue from which this original DEST was isolated) and to a much lesser extent in normal human breast tissue but not in the immortalized breast epithelial cell line B5-589, or in human lung, placenta, uterus and ovary (FIG. 4A). Following amplification using RT/PCR analysis, mammaglobin expression was still not detected in 15 tissues surveyed (FIG. 4B). Detection of glyceraldehyde 3-phosphate dehydrogenase (GAPDH) message (FIG. 4B) and EGF receptor message (data not shown) in these reactions demonstrated that absence of expression was not due to degraded RNA or other trivial explanations. Thus the expression of mammaglobin mRNA is relatively specific for mammary tissue.

EXAMPLE 3

This example demonstrates that the mammaglobin cDNA encodes a translatable nucleotide sequence which results in protein product of appropriately predicted molecular mass. In vitro translations were performed using the TNT™ rabbit reticulocyte translation kit with T7 RNA polymerase (Promega) and 35S-Methionine (>1000 Ci/mmol; 10 mCi/ml, Amersham) according to the manufacturer's protocol.

To 25 μl of TNT™ rabbit reticulocyte lystae was added 2 μl of manufacturer's prepared reaction buffer, T7 RNA polymerase, 20 μM amino acid mixture minus methionine, 40 μCi$^{35}$S-methionine (1,000 Ci/mmol and 10 mCi/ml), 40 units ribonuclease inhibitor, 1 μg of mammaglobin/pGEM7 plasmid, and sufficient DEPC treated water to create a final reaction volume of 50 μl. This reaction was incubated at 30° C. for 60 minutes. 5 μl of this reaction was removed into 20 μl of SDS gel buffer, boiled for 2 minutes, and loaded on a 17.5% SDS-polyacrylamide gel.

Rabbit reticulocyte lysate programmed with mammaglobin cDNA produced a 6 kD protein while that programmed with no cDNA did not produce any protein product.

EXAMPLE 4

This example illustrates the prevalence of overexpression of mammaglobin in primary breast carcinoma.

To determine the frequency of mammaglobin overexpression in breast carcinomas, we examined a panel of fifteen, stage I primary breast carcinomas of differing histological types using Northern blot hybridization with the mammaglobin cDNA probe. Patient-matched normal breast tissues samples were also compared in tissues from two patients (FIG. 6). The 500 bp mammaglobin mRNA was detected in normal breast tissue and tumor 2410 and in three other tumors, two of which when tested demonstrated little or no expression in patient-matched normal tissue (BO15 v. BO16; BO22 v. BO23) (FIG. 6). In all, 4 of 15 (27%) of tumors examined overexpressed mammaglobin mRNA.

These data indicate that overexpression of mammaglobin is not unique to a single tumor specimen and is, in fact, relatively frequent among primary breast tumors. Furthermore, the fact that all tumors examined were stage I suggests that this dysregulation occurs relatively early in the progression of breast neoplasia.

EXAMPLE 5

The following example illustrates the detection of the mammaglobin protein using an anti-mammaglobin polyclonal antibody.

The anti-mammaglobin polyclonal antibody was prepared by coupling a peptide corresponding to the 16 C-terminal amino acids predicted from mammaglobin cDNA (Glu-Val-Phe-Met-Gln-Leu-Ile-Tyr-Asp-Ser-Ser-Leu-Cys-Asp-Leu-Phe, SEQ ID NO:14) to Keyhole Lymphet Hemocyanin and injecting into rabbits with Freund's adjuvant. The inoculated rabbits were boosted at three week intervals and on week 12, the rabbits were bled and the sera was assayed for its ability to detect mammaglobin in serum-free conditioned medium from cultures of the breast tumor cell lines MDA-MB-415 and MCF-7. MDA-MB-415 had been identified earlier as a cell line that overexpresses the mammaglobin message and MCF-7 had been identified as a cell line that produces no detectable mammaglobin mRNA.

The conditioned media was harvested from a 24 hr. culture and resolved on a 12% SDS acrylamide gel under reducing conditions (i.e., the sample was boiled in buffer containing dithiothreitol (DTT) and 2-mercaptoethanol (BME) to reduce disulfide bonds), blotted onto a Nytran filter, and analyzed by standard Western blot protocols using the above described antibody to the C-terminal peptide as the primary antibody in this assay. After primary antibody binding, the blot was washed and secondary antibody (goat anti-rabbit) was added. Mammaglobin-antibody complexes were visualized by enzyme-linked chemiluminescence (ECL Western Blotting Detecting Reagent, Amersham, Arlington Heights, Ill.).

The anti-mammaglobin polyclonal antibody detected a band with an apparent molecular weight of approximately 21 kD in the conditioned media of the MDA-MB-415 cell culture (data not shown). No bands were detected in the conditioned medium of the MCF-7 cell culture (data not shown). Thus, consistent with the mRNA data. MDA-MB-415 cells secrete mammaglobin protein but MCF-7 cells do not.

The apparent molecular weight of the mammaglobin secreted into the MDA-MB-415 culture media is greater than the 10.5 kDa molecular weight calculated from the predicted amino acid sequence of SEQ ID NO:2. Since almost all secreted proteins are glycosylated, the cytosol of MDA-MB-415 cells was analyzed with the anti-mammaglobin polyclonal antibody to see if any precursor forms of secreted mammaglobin could be detected.

MDA-MG-415 cells were grown for 24 hours in serum-free media, the culture media was collected, spun, and the resulting supernatant was collected. The attached cells were washed with phosphate buffered saline (PBS) and lysed with 1×Laemmli sample buffer (2% SDS, 10% glycerol, 100 mM DTT, 60 mM Tris, pH 6.8, 0.001% Bromophenol Blue). The lysis mixture was boiled for 5 minutes and then spun at 10,000 g for 5 minutes to pellet the cell debris. The cell lysate was transferred to a new tube and used for Western blot analysis as described below.

The culture supernatant and cell lysate were run on a 12% SDS acrylamide gel under reducing conditions (i.e., samples boiled in buffer containing DTT and BME) and blotted onto a PVDF membrane using standard techniques. The blot was probed with the polyclonal antibody to the C-terminal peptide in the presence and absence of the competing peptide used to generate the antibody.

Figure 7:
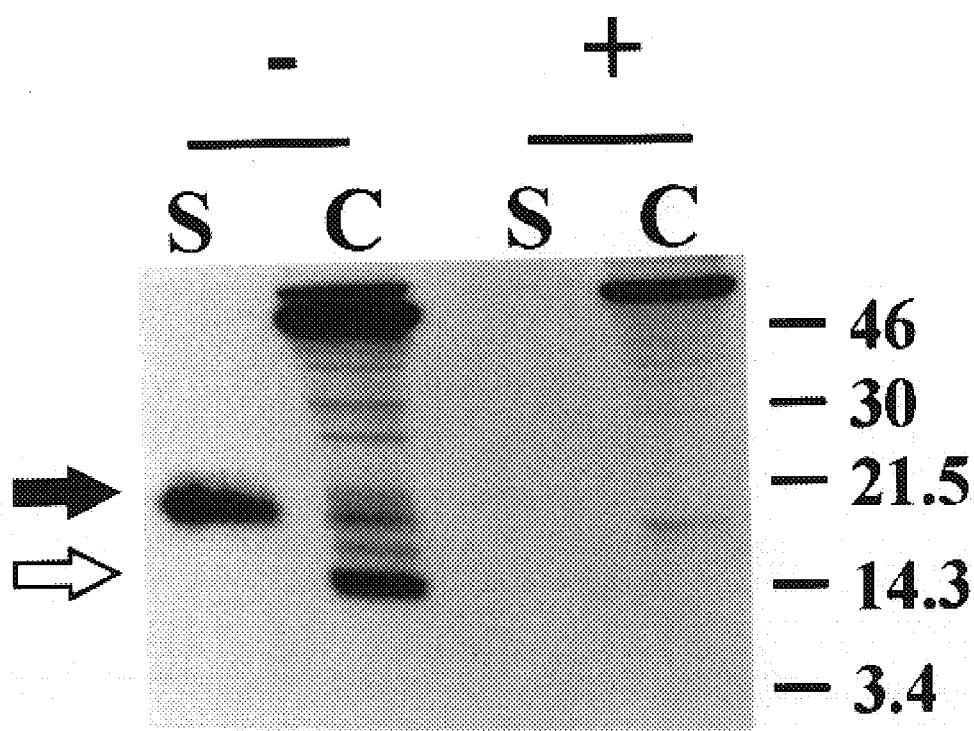
FIG. 7 illustrates the Western blot analysis using polyclonal antibody to the mammaglobin C-terminus (SEQ ID NO:14) of the conditioned medium (S) and cell lysate (C) from MDA-MB-415 breast tumor cells in the absence (−) and presence (+) of the immunizing peptide showing detection of the precursor and secreted forms of mammaglobin protein in the cell medium and cell lysate, respectively.

Visualization of mammaglobin-antibody complexes were as discussed above. As seen in FIG. 7, in the absence of competing peptide (−), the conditioned media (S) has the 21 kD band representative of the secreted mammaglobin protein. The cell lysate (C) showed a prominent band at approximately 14 kD, and several higher molecular weight bands, including one at approximately 21 kD. When the Western blot is performed in the presence of the competing peptide (+), the secreted form and intracellular forms of mammaglobin are not visualized, indicating that these proteins contain the peptide to which the antibody was synthesized.

The 14 kD band detected only in the cell lysate likely represents a precursor, or unprocessed, form of mammaglobin. Since the predicted amino acid sequence for mammaglobin has the consensus N-glycosylation site, Asn-X-Thr, located at residues 53–55 and at residues 68–70 of SEQ ID NO:2, the observed, secreted 21 kD form likely represents some glycosylated form of the protein.

This hypothesis was tested by culturing MDA-MB-415 cells in the presence and absence of tunicamycin, a drug that blocks N-linked glycosylation of eukaryotic proteins. Tunicamycin was added to one of two identical cultures at 1 ug/ml and both cultures were incubated overnight for more hours. The culture media and cell lysate from the treated and control cultures were prepared and analyzed by Western blot analysis as described above.

Figure 8:
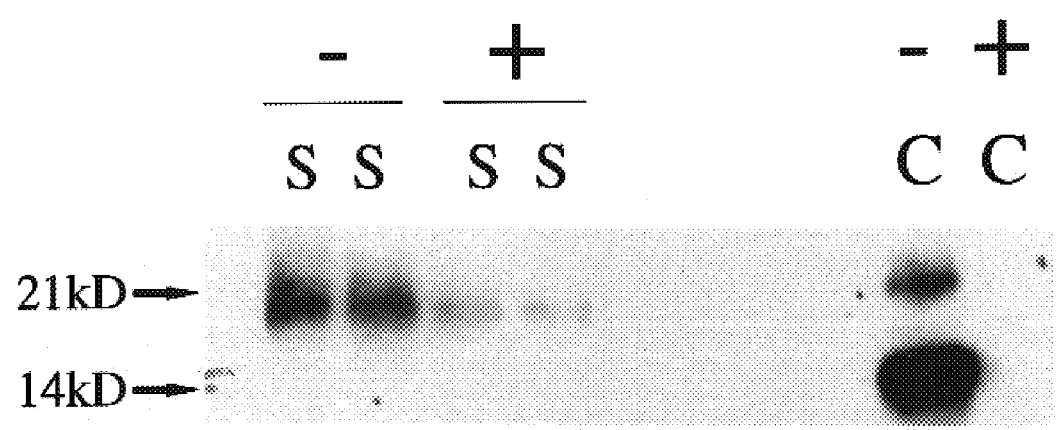
FIG. 8 illustrates the Western blot analysis using the anti-mammaglobin polyclonal antibody of the conditioned medium (S) and cell lysate (C) from MDA-MB-415 breast tumor cells grown in the absence (−) and presence (+) of tunicamycin, which blocks glycosylation, showing the lack of detectable mammaglobin protein in the lysate or medium of cells in which N-linked glycosylation is inhibited.

As shown in FIG. 8, media from cultures (S) treated with tunicamycin (+) lack detectable levels of secreted mammaglobin, suggesting that secreted mammaglobin is glycosylated. Surprisingly, the cell cytosol form of mammaglobin (14 kD) was also not detectable in lysates of MDA-MB-415 cells treated with tunicamycin (far right lane). We hypothesize that blocking early glycosylation events with tunicamycin leads to instability and degradation of precursor forms of mammaglobin, thus explaining the lack of detectable 14 kD protein in the cytosol of tunicamycin-treated cells.

Figure 9:
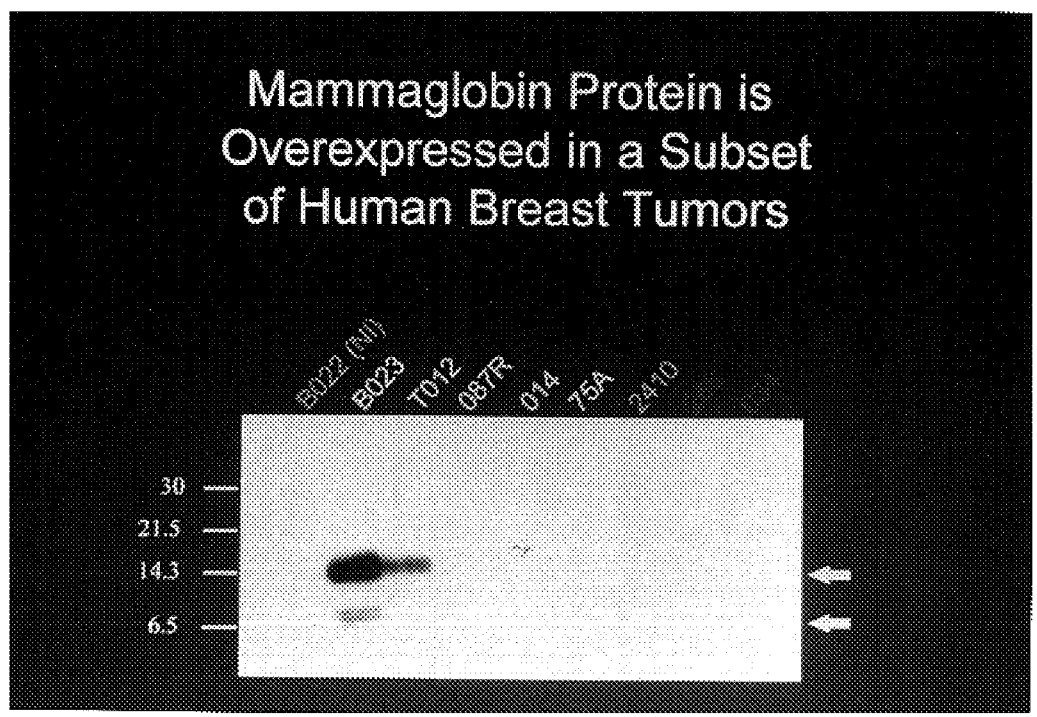
FIG. 9 illustrates the Western blot analysis of cell lysates from human breast tumor cells showing detection of the precursor mammaglobin protein using the anti-mammaglobin polyclonal antibody and goat anti-rabbit antibody visualized by enzyme-linked chemiluminescence.

The polyclonal antibody to the C-terminal peptide of mammaglobin has also detected the 14 kDa precursor form of mammaglobin in cell lysates from primary human breast tumor specimens. As seen in FIG. 9, the precursor form of mammaglobin is present in tumor specimen BO23, but is undetectable in a normal breast tissue sample from the same patient (BO22). Interestingly, some tumor samples that express the mammaglobin transcript (i.e., 087R, 014, 75A and 2410) do not contain detectable levels of mammaglobin protein as assayed by Western blot analysis. One hypothesis consistent with these data is that mammaglobin expression is differentially regulated at the levels of transcription and translation and that this differential regulation is determined the developmental stage of the tumor.

The anti-mammaglobin polyclonal antibody has also been used to look for secreted mammaglobin in breast secretions from proliferating mammary gland. Colostrum or mature milk fluid (500 ul samples) was collected by manual expression from a pregnant woman during the first and third trimester, at birth, and at day 3, 14, and 21 post-partum. The samples were diluted with an equal volume of 2×laemmli sample buffer (4% SDS, 20% glycerol, 200 mM DTT, 120 mM Tris, pH 6.8, 0.002% Bromophenol Blue). The diluted samples were boiled for 5 min. and then spun at 10,000 g for 5 min. at 4° C. to pellet cell debris. The denatured samples were transferred to a new tube and stored at −20° C. prior to Western blot analysis as described above.

Figure 10:
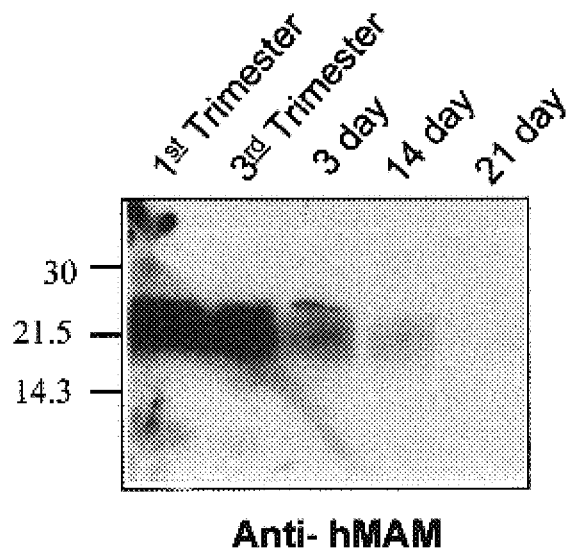
FIG. 10 illustrates the Western blot analysis using the anti-mammaglobin polyclonal antibody of fluid secretions from human breast during pregnancy and postpartum showing detection of the secreted mammaglobin protein in proliferating mammary gland.

As shown in FIG. 10, the antibody detected the 21 kD secreted mammaglobin in breast secretions sampled during pregnancy, a period of high proliferation of breast epithelial cells. However, at the onset of lactation, a stage of breast epithelial differentiation, mammaglobin levels decreased significantly by 3 days post partum and was no longer observed at 14 days post-partum. These results indicate that secreted mammaglobin is associated with proliferating breast epithelial cells, an observation consistent with the detection of secreted mammaglobin in human breast cancer.

Figure 11A:
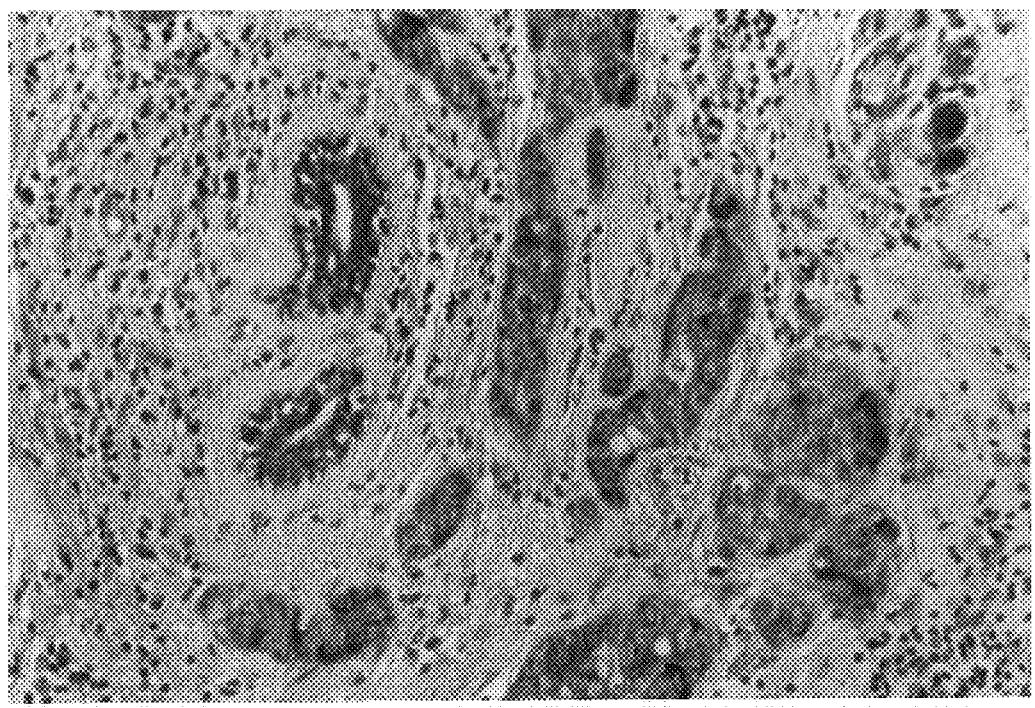
FIG. 11A illustrates in color a paraffin-fixed section of breast cancer cells from a patient specimen immunohistochemically stained using the anti-mammaglobin polyclonal antibody and goat anti-rabbit antibody tagged with horseradish peroxidase and DAB as substrate showing a brown staining of cells expressing the mammaglobin protein.
Figure 11B:
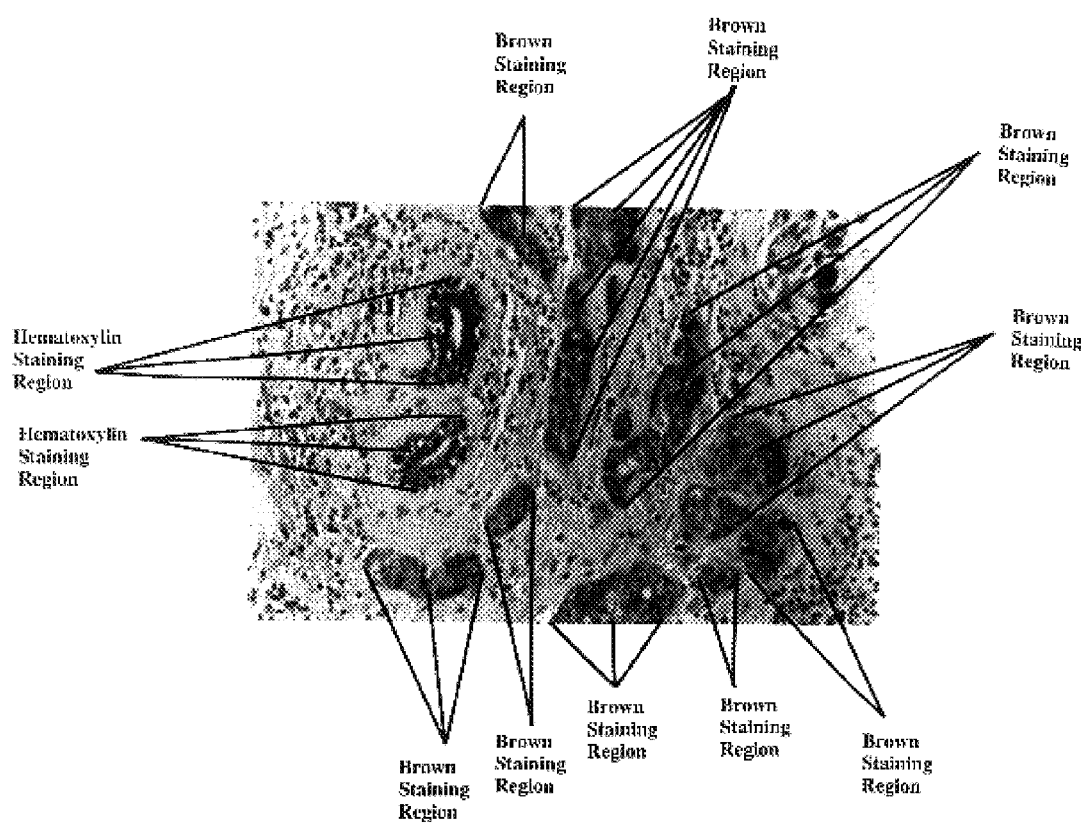
FIG. 11B illustrates in black and white a paraffin-fixed section of breast cancer cell from a patient specimen immunohistochemically stained using the anti-mammaglobin polyclonal antibody and goat anti-rabbit antibody tagged with horseradish peroxidase and DAB as substrate wherein the brown staining of cells expressing the mammaglobin protein is indicated.

Reactivity with the antibody to the mammaglobin peptide has also been shown for breast tumor cells by immunohistochemical staining of paraffin-fixed sections of a breast cancer patient specimen (FIG. 11). The immunohistochemical staining was performed using the antibody to the mammaglobin peptide as the primary antibody and then detecting the mammaglobin-antibody complex using goat anti-rabbit antibody tagged with horseradish peroxidase and 3,3' diamino benzene tetrahydrochloride (DAB) as substrate. Cells expressing the mammaglobin protein showed a brown staining.

From these results, it is believed that the mammaglobin protein is synthesized as a precursor protein and post-translational modifications such as N-linked glycosylation increase its apparent molecular weight prior to secretion; that the stability of precursor forms of mammaglobin is dependent on N-linked glycoslyation: and that mammaglobin protein is secreted by proliferating breast tumor cells. The detection of a mammaglobin protein is applicable in cancer diagnostics using the mammaglobin protein as a breast tumor marker, in assessing breast tumor relapse, in monitoring autologous bone marrow/stem cell transplants for contaminating tumor cells, and in targeting breast tumor cells for therapeutic intervention via antibody-mediated complexes. A purified and isolated mammaglobin polypeptide is useful for generating antibodies against breast tumors and in the development of other tumor-specific immunotherapy regimens.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A composition comprising a mammaglobin fragment, wherein said mammaglobin fragment consists of a sequence of SEQ ID NO:2, mammaglobin, which binds to an antibody specific for SEQ ID NO:2, mammaglobin.

2. The composition of claim 1, wherein said mammaglobin fragment is loaded onto a carrier cell.

3. The composition of claim 1, further comprising a pharmaceutically acceptable adjuvant.

4. The composition of claim 1, wherein said mammaglobin fragment is recognized by a mixture of B cells and $T_c$ cells which recognize SEQ ID NO:2, mammaglobin.

5. The composition of claim 4, wherein said mammaglobin fragment is recognized by B cells and/or $T_c$ cells specific for a naturally occurring, secreted mammaglobin polypeptide which is glycosylated and consists of amino acids 20–93 of SEQ ID NO:2.

6. The composition of claim 5, wherein the mammaglobin fragment is recognized by B cells and/or $T_c$ cells specific for a naturally occurring, secreted mammaglobin polypeptide which is glycosylated and consists of SEQ ID NO:2.

7. The composition of claim 1, wherein the mammaglobin fragment consists of at least 16 contiguous amino acids of SEQ ID NO:2.

8. The composition of claim 7, wherein the mammaglobin fragment consists of at least 25 contiguous amino acids of SEQ ID NO:2.

9. The composition of claim 8, wherein the mammaglobin fragment is glycosylated and consists of amino acids 20–93 of SEQ ID NO:2.

10. The composition of claim 9, wherein the mammaglobin fragment is glycosylated and consist of SEQ ID NO:2.

11. The composition of claim 4, wherein the mammaglobin fragment induces in vitro activation and expansion of B cells that are specific for SEQ ID NO:2, wherein the B cells are isolated from a breast cancer sample.

12. The composition of claim 4, wherein the mammaglobin fragment induces in vitro activation and expansion of $T_c$ cells that are specific for SEQ ID NO:2, wherein the $T_c$ cells are isolated from a breast cancer sample.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 503 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 1:

```
GACAGCGGCT TCCTTGATCC TTGCCACCCG CGACTGAACA CCGACAGCAG CAGCCTCACC        60

ATGAAGTTGC TGATGGTCCT CATGCTGGCG GCCCTCTCCC AGCACTGCTA CGCAGGCTCT       120

GGCTGCCCCT TATTGGAGAA TGTGATTTCC AAGACAATCA ATCCACAAGT GTCTAAGACT       180

GAATACAAAG AACTTCTTCA AGAGTTCATA GACGACAATG CCACTACAAA TGCCATAGAT       240

GAATTGAAGG AATGTTTTCT TAACCAAACG GATGAAACTC TGAGCAATGT TGAGGTGTTT       300

ATGCAATTAA TATATGACAG CAGTCTTTGT GATTTATTTT AACTTTCTGC AAGACCTTTG       360

GCTCACAGAA CTGCAGGGTA TGGTGAGAAA CCAACTACGG ATTGCTGCAA ACCACACCTT       420

CTCTTTCTTA TGTCTTTTTA CTACAAACTA CAAGACAATT GTTGAAACCT GCTATACATG       480

TTTATTTTAA TAAATTGATG GCA                                               503
```

(2) INFORMATION FOR SEQ ID NO: 2:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 2:

```
Met Lys Leu Leu Met Val Leu Met Leu Ala Ala Leu Ser Gln His Cys
 1               5                  10                  15

Tyr Ala Gly Ser Gly Cys Pro Leu Leu Glu Asn Val Ile Ser Lys Thr
            20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
    50                  55                  60

Cys Phe Leu Asn Gln Thr Asp Glu Thr Leu Ser Asn Val Glu Val Phe
65                  70                  75                  80

Met Gln Leu Ile Tyr Asp Ser Ser Leu Cys Asp Leu Phe
                85                  90
```

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 3:

```
CAGCGGCTTC CTTGATCCTT G                                                  21
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

ATAAGAAAGA GAAGGTGTGG                                                    20

(2) INFORMATION FOR SEQ ID NO: 5:

(i) SEQUENCE CHARACTERISTICS:
            (A) LENGTH: 403 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 5:

GACAGCGGCT TCCTTGATCC TTGCCACCCG CGACTGAACA CCGACAGCAG CAGCCTCACC          60

ATGAAGTTGC TGATGGTCCT CATGCTGGCG GCCCTCTCCC AGCACTGCTA CGCAGGCTCT        120

GGCTGCCCCT TATTGGAGAA TGTGATTTCC AAGACAATCA ATCCACAAGT GTCTAAGACT        180

GAATACAAAG AACTTCTTCA AGAGTTCATA GACGACAATG CCACTACAAA TGCCATAGAT        240

GAATTGAAGG AATGTTTTCT TAACCAAACG GATGAAACTC TGAGCAATGT TGAGGTGTTT        300

ATGCAATTAA TATATGACAG CAGTCTTTGT GATTTATTTT AACTTTCTGC AAGACCTTTG        360

GCTCACAGAA CTGCAGGGTA TGGTGAGAAA CCAACTACGG ATT                          403

(2) INFORMATION FOR SEQ ID NO: 6:

(i) SEQUENCE CHARACTERISTICS:
            (A) LENGTH: 206 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 6:

TTTATGCAAT TAATATATGA CAGCAGTCTT TGTGATTTAT TTTAACTTTC TGCAAGACCT         60

TTGGCTCACA GAACTGCAGG GTATGGTGAG AAACCAACTA CGGATTGCTG CAAACCACAC        120

CTTCTCTTTC TTATGTCTTT TTACTACAAA CTACAAGACA ATTGTTGAAA CCTGCTATAC        180

ATGTTTATTT TAATAAATTG ATGGCA                                             206

(2) INFORMATION FOR SEQ ID NO: 7:

(i) SEQUENCE CHARACTERISTICS:
            (A) LENGTH: 95 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO: 7:

Met Lys Leu Val Phe Leu Phe Leu Leu Val Thr Ile Pro Ile Cys Cys
1               5                   10                  15

Tyr Ala Ser Gly Ser Gly Cys Ser Ile Leu Asp Glu Val Ile Arg Gly
                20                  25                  30

Thr Ile Asn Ser Thr Val Thr Leu His Asp Tyr Met Lys Leu Val Lys
            35                  40                  45

Pro Tyr Val Gln Asp His Phe Thr Glu Lys Ala Val Lys Gln Phe Lys
        50                  55                  60

Gln Cys Phe Leu Asp Gln Thr Asp Lys Thr Leu Glu Asn Val Gly Val
65                  70                  75                  80

Met Met Glu Ala Ile Phe Asn Ser Glu Ser Cys Gln Gln Pro Ser
                85                  90                  95

(2) INFORMATION FOR SEQ ID NO: 8:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 8:

Met Lys Leu Ala Val Thr Leu Thr Leu Val Thr Leu Ala Leu Cys Cys
1               5                   10                  15

Ser Ser Ala Ser Ala Glu Ile Cys Pro Ser Phe Gln Arg Val Ile Glu
                20                  25                  30

Thr Leu Leu Met Asp Thr Pro Ser Ser Tyr Glu Ala Ala Met Glu Leu
            35                  40                  45

Phe Ser Pro Asp Gln Asp Met Arg Glu Ala Gly Ala Gln Leu Lys Lys
        50                  55                  60

Leu Val Asp Thr Leu Pro Gln Lys Pro Arg Glu Ser Ile Ile Lys Leu
65                  70                  75                  80

Met Glu Lys Ile Ala Gln Ser Ser Leu Cys Asn
                85                  90

(2) INFORMATION FOR SEQ ID NO: 9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 9:

CACGAATTCA CTATCGATTC TGGAACCTTC AGAGG                                    35

(2) INFORMATION FOR SEQ ID NO: 10:

(i) SEQUENCE CHARACTERISTICS:
        (A) LENGTH: 38 base pairs
        (B) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

CTGGTTCGGC CCACCTCTGA AGGTTCCAGA ATCGATAG                                38

(2) INFORMATION FOR SEQ ID NO: 11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 11:

AATCCGTAGT TGGTTTCTCA CC                                                 22

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 12:

CTTTCTGCAA GACCTTTGGC                                                    20

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 13:

TTTTTTTTTT TTTTTTTTT T                                                   21

(2) INFORMATION FOR SEQ ID NO: 14:

(i) SEQUENCE CHARACTERISTICS:
        (A) LENGTH: 16 amino acids
        (B) TYPE: amino acid
        (C) STRANDEDNESS: single
        (D) TOPOLOGY: linear -continued

```
    (ii) MOLECULE TYPE: peptide (iii) HYPOTHETICAL: NO (xi) SEQUENCE DESCRIPTION: SEQ ID NO: 14:

Glu Val Phe Met Gln Leu Ile Tyr Asp Ser Ser Leu Cys Asp Leu Phe
1               5                  10                  15
```